US011154183B2

(12) United States Patent
Yeung et al.

(10) Patent No.: US 11,154,183 B2
(45) Date of Patent: Oct. 26, 2021

(54) SINGLE ACCESS SURGICAL ROBOTIC DEVICES AND SYSTEMS, AND METHODS OF CONFIGURING SINGLE ACCESS SURGICAL ROBOTIC DEVICES AND SYSTEMS

(71) Applicant: Bio-Medical Engineering (HK) Limited, Hong Kong (CN)

(72) Inventors: Chung-Kwong Yeung, Hong Kong (CN); Kai-Leung Yung, Hong Kong (CN); Jimmy Tsun-Ping To, Hong Kong (CN)

(73) Assignee: Bio-Medical Engineering (HK) Limited, Hong Kong (CN)

( * ) Notice: Subject to any disclaimer, the term of this patent is extended or adjusted under 35 U.S.C. 154(b) by 0 days.

(21) Appl. No.: 14/693,207

(22) Filed: Apr. 22, 2015

(65) Prior Publication Data
US 2015/0297299 A1 Oct. 22, 2015

Related U.S. Application Data

(60) Provisional application No. 61/982,717, filed on Apr. 22, 2014.

(51) Int. Cl.
*A61B 1/00* (2006.01)
*A61B 17/34* (2006.01)
(Continued)

(52) U.S. Cl.
CPC ........ *A61B 1/00147* (2013.01); *A61B 1/0016* (2013.01); *A61B 1/00133* (2013.01);
(Continued)

(58) Field of Classification Search
CPC ............ A61B 1/00131; A61B 1/00133; A61B 1/00135; A61B 1/00137; A61B 1/0014;
(Continued)

(56) References Cited

U.S. PATENT DOCUMENTS

| 5,342,254 A | 8/1994 | Sula |
| 10,105,128 B2 | 10/2018 | Cooper et al. |

(Continued)

FOREIGN PATENT DOCUMENTS

| CA | 2720572 A1 | 6/2011 |
| CN | 201135461 Y | 10/2008 |

(Continued)

OTHER PUBLICATIONS

International Search Report of the International Seaching Authority for co-pending international application No. PCT/CN2015/000284, dated Jul. 14, 2015.

(Continued)

*Primary Examiner* — Ryan N Henderson
(74) *Attorney, Agent, or Firm* — Baker & McKenzie LLP

(57) ABSTRACT

Example embodiments relate to devices, systems, and methods for performing a surgical action. The device may comprise a port assembly, a camera arm assembly, and an instrument arm assembly. The port assembly comprises an access port and a plurality of anchoring portions. The camera arm assembly comprises at least one camera at a distal end and is configurable to insert into the access port and attach to one of the anchoring portions. The instrument arm assembly comprises a serial arrangement including a plurality of arm segments, a plurality of joint portions, and at least one end instrument attached to one of the arm segments by an instrument joint portion at a distal end. Each joint portion is configurable to provide an attached arm segment with at least one degree of freedom. Furthermore, the instrument joint portion is configurable to provide the end instrument with at least one degree of freedom.

15 Claims, 24 Drawing Sheets

(51) Int. Cl.
  *A61B 34/30* (2016.01)
  *A61B 34/37* (2016.01)
  *A61B 34/00* (2016.01)
  *A61B 90/00* (2016.01)
  A61B 1/313 (2006.01)
  A61B 1/05 (2006.01)
  A61B 90/30 (2016.01)
  A61B 17/00 (2006.01)

(52) U.S. Cl.
  CPC ...... *A61B 1/00149* (2013.01); *A61B 17/3421* (2013.01); *A61B 17/3423* (2013.01); *A61B 34/30* (2016.02); *A61B 34/37* (2016.02); *A61B 34/76* (2016.02); *A61B 90/361* (2016.02); *A61B 1/05* (2013.01); *A61B 1/3132* (2013.01); *A61B 17/00234* (2013.01); *A61B 90/30* (2016.02); *A61B 2017/3445* (2013.01); *A61B 2034/305* (2016.02); *Y10S 901/02* (2013.01); *Y10S 901/27* (2013.01)

(58) Field of Classification Search
  CPC ............ A61B 1/00147; A61B 1/00149; A61B 1/00154; A61B 1/0016; A61B 1/01; A61B 1/005; A61B 1/0051; A61B 1/0052; A61B 1/0053; A61B 1/0055; A61B 1/0056; A61B 1/0057; A61B 1/0058; A61B 1/008; A61B 1/313; A61B 1/317; A61B 17/3421; A61B 17/3423; A61B 34/30; A61B 34/32; A61B 34/35; A61B 34/37; A61B 34/70; A61B 34/71; A61B 34/72; A61B 34/73; A61B 34/74; A61B 34/76; A61B 2034/305
  USPC ........ 600/104, 106, 107, 114–116, 184–246; 606/1, 130
  See application file for complete search history.

(56) References Cited

U.S. PATENT DOCUMENTS

| | | | |
|---|---|---|---|
| 2005/0096502 A1* | 5/2005 | Khalili | A61B 1/018 600/106 |
| 2005/0203342 A1 | 9/2005 | Kucklick et al. | |
| 2007/0123855 A1 | 5/2007 | Morley et al. | |
| 2007/0156019 A1* | 7/2007 | Larkin | B25J 19/025 600/104 |
| 2007/0175961 A1 | 8/2007 | Shelton, IV et al. | |
| 2007/0287884 A1 | 12/2007 | Schena | |
| 2008/0039255 A1 | 2/2008 | Jinno et al. | |
| 2008/0065099 A1* | 3/2008 | Cooper | A61B 1/00087 606/130 |
| 2008/0065110 A1 | 3/2008 | Duval et al. | |
| 2009/0326318 A1 | 12/2009 | Tognaccini et al. | |
| 2010/0331857 A1 | 12/2010 | Doyle et al. | |
| 2011/0202068 A1 | 8/2011 | Diolaiti et al. | |
| 2011/0213384 A1 | 9/2011 | Jeong | |
| 2012/0022553 A1 | 1/2012 | Cooper et al. | |
| 2012/0035416 A1 | 9/2012 | Fernandez et al. | |
| 2012/0232339 A1* | 9/2012 | Csiky | A61B 17/07207 600/104 |
| 2012/0279343 A1 | 11/2012 | Ihrke et al. | |
| 2013/0131695 A1* | 5/2013 | Scarfogliero | A61B 19/2203 606/130 |
| 2013/0144395 A1 | 6/2013 | Stefanchik et al. | |
| 2013/0289579 A1 | 10/2013 | Yeung et al. | |
| 2013/0289768 A1* | 10/2013 | Yeung | A61B 17/3417 700/258 |
| 2013/0317521 A1 | 11/2013 | Choi et al. | |
| 2014/0051934 A1 | 2/2014 | Ma et al. | |
| 2014/0128882 A1* | 5/2014 | Kwak | A61B 34/30 606/130 |
| 2014/0142377 A1* | 5/2014 | Yang | A61B 90/30 600/104 |
| 2014/0257331 A1* | 9/2014 | Kim | A61B 34/37 606/130 |
| 2014/0257336 A1* | 9/2014 | Choi | A61B 1/0055 606/130 |
| 2014/0350337 A1 | 11/2014 | Simaan et al. | |
| 2015/0051446 A1 | 2/2015 | Farritor et al. | |
| 2016/0135898 A1 | 5/2016 | Frederick et al. | |
| 2016/0157948 A1 | 6/2016 | Yeung | |
| 2019/0060015 A1 | 2/2019 | Yeung et al. | |
| 2019/0314100 A1 | 10/2019 | Yeung et al. | |
| 2019/0321119 A1 | 10/2019 | Yeung et al. | |

FOREIGN PATENT DOCUMENTS

| | | |
|---|---|---|
| CN | 101500470 A | 8/2009 |
| CN | 101791247 A1 | 8/2010 |
| CN | 101999938 A | 4/2011 |
| CN | 201968771 U | 9/2011 |
| CN | 102274077 A | 12/2011 |
| CN | 202637006 U | 1/2013 |
| CN | 103431913 A | 12/2013 |
| CN | 103582462 A | 2/2014 |
| CN | 1004224324 A | 12/2014 |
| CN | 104582594 A | 4/2015 |
| CN | 104883991 A | 9/2015 |
| CN | 105358072 A | 2/2016 |
| CN | 105583819 A | 5/2016 |
| CN | 105816242 A | 8/2016 |
| CN | 105832418 A | 8/2016 |
| CN | 106562806 A | 4/2017 |
| CN | 106999251 A | 8/2017 |
| CN | 107440799 A | 12/2017 |
| CN | 107485415 A | 12/2017 |
| CN | 107616840 A | 1/2018 |
| CN | 107661144 A | 2/2018 |
| CN | 107848119 A | 3/2018 |
| CN | 107961078 A | 4/2018 |
| CN | 108697474 A | 10/2018 |
| CN | 109567943 A | 4/2019 |
| CN | 109715081 A | 5/2019 |
| CN | 109890580 A | 6/2019 |
| CN | 110478043 A | 11/2019 |
| CN | 110547876 A | 12/2019 |
| EP | 3501413 A1 | 6/2019 |
| WO | 9510241 | 4/1995 |
| WO | 2007146987 A3 | 12/2007 |
| WO | 2010151438 A1 | 12/2010 |
| WO | 2011135503 A1 | 11/2011 |
| WO | 2016/059369 A1 | 4/2016 |

OTHER PUBLICATIONS

Written Opinion of the International Searching Authority for co-pending international application No. PCT/CN2015/000284, dated Jul. 14, 2015.
A first Office Action from the PRC Patent Office dated Apr. 13, 2017 in connections with Chinese Patent Application No. 201580000449.0.
Extended European Search Report dated Sep. 12, 2018 in corresponding European patent application 16782509.0; 9 pages.
An International Search Report and Written Opinion dated Aug. 25, 2017 in corresponding International patent application PCT/CN2017/086204.
Office Action issued in connection with European Patent Application No. 15782679.3 dated Jan. 23, 2018, 8 pages.
Office Action issued in connection with Chinese Patent Application No. 201610257789.8 dated Nov. 1, 2017, 11 pages.
European Examination Report dated Dec. 11, 2018 in connection with European patent application 16782509.0; 8 pages.
Marco Piccigallo et al., "Design of a Novel Bimanual Robotic System for Single-Port Laparoscopy", IEEE/ ASME Transactions on Mechatronics, IEEE Service Center, Piscataway, New Jersey, vol. 15, No. 6, Dec. 1, 2010, pp. 871-878.

(56) References Cited

OTHER PUBLICATIONS

International Search Report dated Mar. 28, 2019 in connection with International Application No. PCT/CN2018/099830, 7 pages.
Written Opinion of the International Searching Authority dated Mar. 28, 2019 in connection with International Application No. PCT/CN2018/099830, 4 pages.
Office Action dated Apr. 1, 2020 in connection with Chinese Application No. 201910749646.2, 5 pages.
International Search Report and Written Opinion dated Mar. 26, 2020 in connection with International Application No. PCT/CN2019/096204, 10 pages.
International Search Report and Written Opinion dated Mar. 26, 2020 in connection with International Application No. PCT/CN2019/096199, 11 pages.
Examination Report dated Jan. 28, 2020 in connection with Indian Application No. 201617017442, 7 pages.
Examination Report dated Dec. 10, 2019 in connection with Indian Application No. 201717002757, 5 pages.
Examination Report dated Feb. 6, 2020 in connection with Indian Application No. 201817034862, 6 pages.
First Office Action dated Mar. 19, 2020 in connection with Chinese Application No. 201910749590.0, 7 pages.
First Office Action dated Aug. 5, 2020 in connection with Chinese Application No. 201810337515.9, 11 pages.
First Examination Report dated Jun. 23, 2020 in connection with Indian Application No. 201817037446, 6 pages.
Third Office Action dated Jun. 22, 2020 in connection with Chinese Application No. 201710714234.6, 8 pages.
First Examination Report dated Apr. 27, 2020 in connection with Indian Application No. 201817037452, 7 pages.
Chinese Office Action dated Jul. 8, 2019 in connection with Chinese Application No. 201710714234.6, 13 pages.
Chinese Office Action dated Jul. 4, 2019 in connection with Chinese Application No. 201710713625.6, 10 pages.
Chinese Office Action dated Jul. 8, 2019 in connection with Chinese Application No. 201710713638.3, 13 pages.

\* cited by examiner

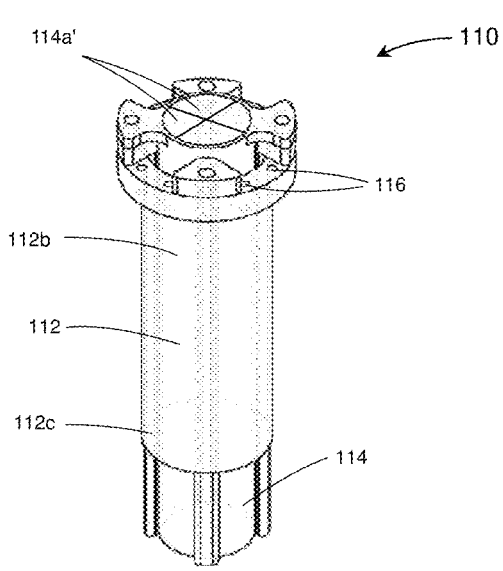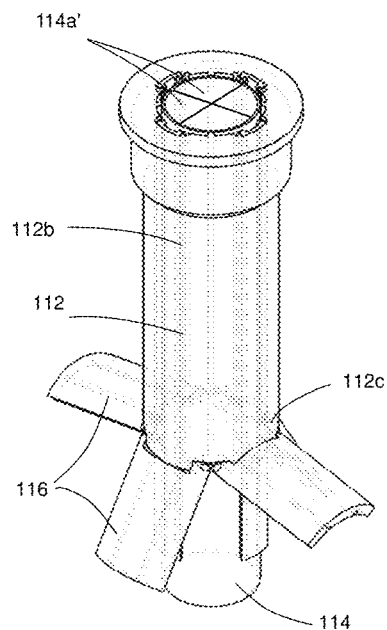
FIGURE 6H  FIGURE 6I
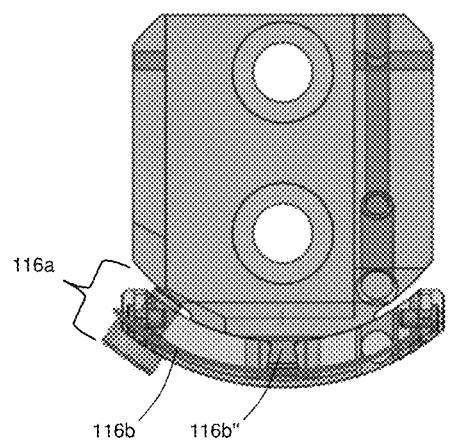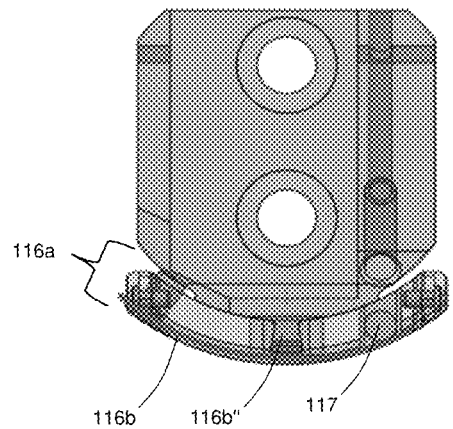
FIGURE 6J  FIGURE 6K

SINGLE ACCESS SURGICAL ROBOTIC DEVICES AND SYSTEMS, AND METHODS OF CONFIGURING SINGLE ACCESS SURGICAL ROBOTIC DEVICES AND SYSTEMS

This application claims priority to U.S. Provisional Application No. 61/982,717, filed on Apr. 22, 2014, which application is incorporated herein by reference in its entirety.

BACKGROUND

The present disclosure relates generally to surgical systems, devices, and methods, and more specifically, relates to systems and devices for use in performing Minimally Invasive Surgical (MIS) procedures, and methods of configuring such surgical systems and devices.

With the advancement of medical science and technology, most conventional open surgical procedures, which require large incisions to a patient in order to view and access inside the body cavity of the patient, have been largely replaced with MIS procedures. Computer-assisted and/or robotic surgical technology has contributed to advancements in MIS so as to translate a surgeon's desired actions, including movements of the surgeon's fingers and hands, into movements of laparoscopic instruments inside the body cavity of a patient.

BRIEF SUMMARY

Despite recent developments in modern medical science, it is recognized in the present disclosure that one or more problems are encountered in modern surgical technology and methodology, including MIS. For example, a typical MIS procedure requires multiple incisions to a patient in order to allow access via the incisions for the insertion of a camera and various other laparoscopic instruments into the body cavity of the patient.

As another example, it is recognized in the present disclosure that surgical robotic devices, including surgical robotic arms, oftentimes encounter difficulties during surgical procedures due to insufficient anchoring and/or reactive forces to stabilize against forces that are desired and/or necessary to be applied during surgical actions.

It is also recognized in the present disclosure that surgical robotic systems face difficulties in providing an instrument, such as a cutting or gripping instrument attached to the end of a surgical robotic arm, with access to all or even most parts, areas, and/or quadrants of abdominal cavity of a patient. That is, after the surgical robotic arm is inserted in the abdominal cavity of the patient and ready to perform a surgical action, the instrument attached to the end of the surgical robotic arm is typically limited to access only certain parts, areas, and quadrants of the abdominal cavity of the patient.

In yet another example of a problem encountered by surgical robotic systems, surgical robotic systems typically provide only between one to two surgical robotic arms per access or opening (such as an incision or a natural orifice) of the patient. In this regard, one or more additional incisions will be required for the insertion of a camera and various laparoscopic instruments into the abdominal cavity of the patient.

Present example embodiments relate generally to systems, devices, and methods for addressing one or more problems in surgical robotic systems, devices, and methods, including those described above and herein.

In an exemplary embodiment, a surgical robotic device is described in the present disclosure comprising a port assembly, a camera arm assembly, and an instrument arm assembly. The port assembly comprises an access port and a plurality of anchoring portions. The camera arm assembly comprises at least one camera at a distal end and the camera arm assembly is configurable to insert into the access port and attach to one of the anchoring portions. The instrument arm assembly comprises a serial arrangement including a plurality of arm segments, a plurality of joint portions, and at least one end instrument attached to one of the arm segments by an instrument joint portion at a distal end. Each joint portion is configurable to provide an attached arm segment with at least one degree of freedom. Furthermore, the instrument joint portion is configurable to provide the end instrument with at least one degree of freedom. Furthermore, the instrument arm assembly is configurable to provide at least seven in vivo degrees of freedom. Furthermore, the instrument arm assembly is configurable to insert into the access port and attach to one of the anchoring portions.

In another exemplary embodiment, a surgical device is described in the present disclosure comprising a port assembly, an instrument arm assembly, and a camera arm assembly. The port assembly comprises an outer body and an inner body. The outer body comprises a first access port, a first end, a second end, and a plurality of anchoring portions. The first end is fixably positionable in at least a portion of an opening of a patient in one of a plurality of positions. The second end is operable to attach to an external anchor. The inner body is fixably positionable in the first access port to form a second access port. The instrument arm assembly is configurable in a serial arrangement including a plurality of arm segments, a plurality of joint portions, and at least one end instrument attached to one of the arm segments by an instrument joint portion at a distal end. The instrument arm assembly is configurable to attach to one of the anchoring portions. The camera arm assembly comprises at least one camera at a distal end, and the camera arm assembly is configurable to attach to one of the anchoring portions. The port assembly is configurable to provide at least one degree of freedom. The port assembly is configurable to allow an insertion of the instrument arm assembly and the camera arm assembly into the abdominal cavity of a patient via the first access port. Furthermore, the port assembly is configurable to allow an insertion of equipment into the abdominal cavity of the patient via the second access port when the surgical device is in operation.

In another exemplary embodiment, a method for configuring a surgical device for performing a surgical action in the abdominal cavity of a patient is described in the present disclosure. The method comprises providing an external anchor and a port assembly having an outer body member and an inner body member. The method further comprises providing a camera arm assembly, the camera arm assembly having a serial arrangement including a plurality of camera arm segments, a plurality of camera joint portions, and at least one camera attached to one of the camera arm segments. In this regard, each camera joint portion is configurable to provide an attached camera arm segment with at least one degree of freedom. The method further comprises providing a plurality of instrument arm assemblies, each instrument arm assembly having a serial arrangement including a plurality of arm segments, a plurality of joint portions, and at least one end instrument attached to one of the arm segments at a distal end. In this regard, each joint portion is configurable to provide an attached arm segment with at least two degrees of freedom. The method further comprises positioning the outer body member in at least a portion of an opening of a patient in one of a plurality of positions using the external anchor. The method further comprises inserting the camera arm assembly into the abdominal cavity of the patient via a first port of the outer body member, and dynamically configuring one or more of the camera joint portions in such a way as to prevent a portion of the camera arm assembly from contacting with the inner wall of the abdominal cavity of the patient and to provide a clear passageway into the abdominal cavity of the patient via the first port. The method further comprises attaching the camera arm assembly to the outer body member. The method further comprises inserting one of the instrument arm assemblies into the abdominal cavity of the patient via the first port of the outer body member, and dynamically configuring one or more of the joint portions in such a way as to prevent a portion of the instrument arm assembly from contacting with the inner wall of the abdominal cavity of the patient and to provide a clear passageway into the abdominal cavity of the patient via the first port. The method further comprises attaching the inserted instrument arm assembly to the outer body member. The method further comprises repeating the inserting and dynamic configuring of the instrument arm assembly for one or more other instrument arm assemblies. The method further comprises securing the inner body member into the first port of the outer body member to form a second port. The method further comprises inserting one or more surgical equipment into the second port.

BRIEF DESCRIPTION OF THE DRAWINGS

For a more complete understanding of the present disclosure, example embodiments, and their advantages, reference is now made to the following description taken in conjunction with the accompanying drawings, in which like reference numbers indicate like features, and:

FIG. 6H is an illustration of a perspective view of an example embodiment of a port assembly having an air shutter;

FIG. 6I is an illustration of a perspective view of another example embodiment of a port assembly having an air shutter;

FIG. 6J is an illustration of a cross sectional view of an example embodiment of a spring lock engaged in a locked position;

FIG. 6K is an illustration of a cross sectional view of an example embodiment of a spring lock engaged in an unlocked position;

Although similar reference numbers may be used to refer to similar elements in the figures for convenience, it can be appreciated that each of the various example embodiments may be considered to be distinct variations.

DETAILED DESCRIPTION

Figure 1:
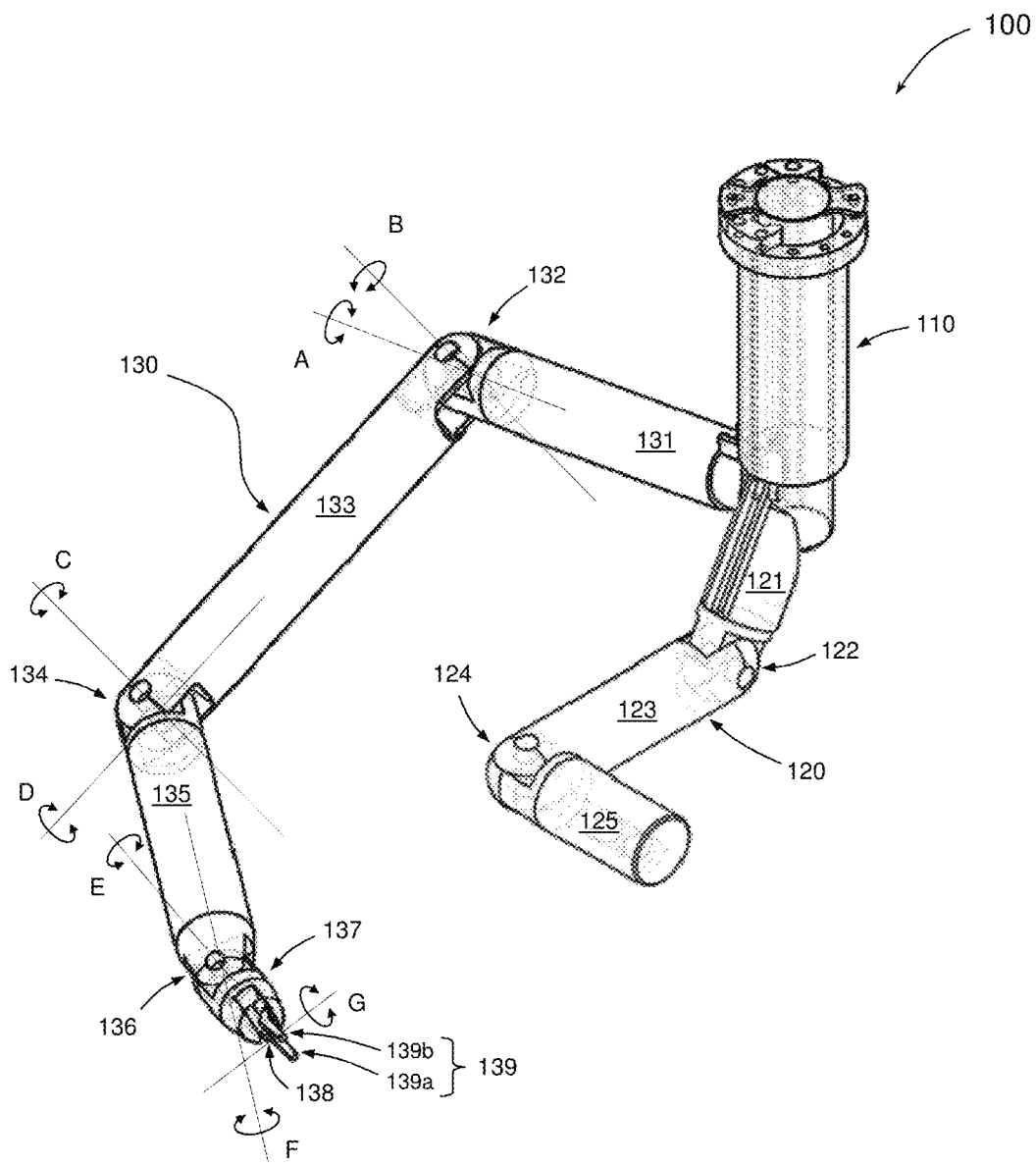
FIG. 1 is an illustration of a perspective view of an example embodiment of a surgical device configured with one port assembly, one instrument arm assembly, and one camera arm assembly.

Example embodiments will now be described with reference to the accompanying drawings, which form a part of the present disclosure, and which illustrate example embodiments which may be practiced. As used in the present disclosure and the appended claims, the terms "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an" and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and the appended claims, the words "and/or" may refer to and encompass any and all possible combinations of one or more of the associated listed items.

It is recognized in the present disclosure that, despite recent developments in medical science and technology, one or more problems are encountered in surgical technology and methodology, including MIS. For example, a typical MIS procedure requires multiple incisions or a single incision of up to 35 mm each to a patient in order to allow access for the insertion of a camera and various other laparoscopic instruments into the abdominal cavity of the patient. It is recognized in the present disclosure that such rather large and multiple incisions impose several in-surgery and post-surgery disadvantages, undesirable consequences, and/or complications to the patient, including excessive blood loss, large and multiple wound/scar sizes, and longer healing times, thereby necessitating longer hospitalization periods.

In addition to the aforementioned disadvantages pertaining to the multiple and rather large incisions, it is recognized in the present disclosure that surgical robotic systems, including surgical robotic arms (and those instruments attached to them), developed for performing robotic-assisted MIS surgical procedures also suffer from one or more problems. For example, it is recognized herein that a major technical challenge for a surgical robotic system is the difficulty in providing sufficient anchoring and/or reactive forces to stabilize against forces that are desired and/or necessary to be applied to the patient by the surgical robotic system during a surgical action. In this regard, certain surgical actions for known surgical robotic systems may require tremendous effort and time, and may not be performed properly or at all as a result of the problem of insufficient anchoring and/or reactive forces.

Another example of a problem recognized in the present disclosure as being encountered by surgical robotic systems is the difficulty in providing an instrument, such as a cutting and/or gripping instrument attached to the end of a surgical robotic arm, with access to all or even most parts, areas, and quadrants of an abdominal cavity of a patient after the surgical robotic system has been set up (or installed) and is ready to perform a surgery. That is, after the surgical robotic arm of the system has been inserted, attached, and properly set up in the abdominal cavity of the patient and is ready to perform a surgical action, the instrument attached to the end of the surgical robotic arm is typically limited to access only certain parts, areas, and quadrants of the abdominal cavity of the patient. It is recognized in the present disclosure that such problems result in large from the limited number of possible degrees of freedom that can be provided by known surgical robotic systems and arms, and more specifically, the limited number of in vivo degrees of freedom (i.e. the degrees of freedom provided within an abdominal cavity of a patient) of known surgical robotic systems and arms. In this regard, surgical robotic systems typically provide only between 2 to 4 in vivo degrees of freedom for each surgical robotic arm.

Recent developments to surgical robotic systems attempt to solve the aforementioned problem by providing an additional in vitro degree of freedom (i.e. the degree of freedom provided from outside the body of a patient). It is recognized in the present disclosure, however, that such recent developments still do not sufficiently address the difficulties in providing an instrument attached to the end of a surgical robotic arm with access to all parts, areas, and/or quadrants of the abdominal cavity of the patient after the surgical robotic system has been set up and is ready to perform a surgical action in the abdominal cavity of the patient.

As another example, surgical robotic systems typically only provide for between one to two surgical robotic arms per access or opening (such as an incision or a natural orifice) of the patient. In this regard, when additional laparoscopic instruments, such as another surgical robotic arm, a suction tube, and/or a camera, are required to be inserted into the abdominal cavity of the patient, one or more additional openings (incisions) are required for the patient.

In respect to surgical robotic arms, surgical teams often encounter difficulties with properly inserting and removing surgical robotic arms into and out of a body cavity of the patient. Specifically, since surgical robotic arms generally have at least one joint and two arm segments, the insertion of a surgical robotic arm into the body cavity oftentimes results in a portion of the surgical robotic arm (such as the end connected to an instrument, such as a cutting tool) coming into contact with and damaging patient tissue. Likewise, the removal of a surgical robotic arm from the body cavity oftentimes results in a portion of the surgical robotic arm coming into contact with and damaging patient tissue. This problem becomes compounded when a surgical procedure or system attempts to employ more than one surgical robotic arm through a single port.

It is also recognized in the present disclosure that surgical robotic systems oftentimes face problems in respect to the heating up of one or more components during a surgical action, such as the heating up of laparoscopic optics (such as a camera), lighting elements, and other components. For example, the increased temperature of such components may possibly impose in-surgery and/or post-surgery damage or complications to patient tissues that come into contact with such components.

In yet another example problem, surgical procedures and systems oftentimes encounter problems with providing and maintaining sufficient insufflation of a body cavity (such as an abdominal cavity) throughout a surgical procedure.

Another example problem encountered by surgical procedures and systems pertains to the tendency for laparoscopic optics (such as a lens of a camera) and/or lighting elements to encounter contamination and/or partial or complete blockage during a surgical procedure due to fogging, tissue debris, liquids (such as blood), and/or other particles accumulated before, during, and/or after insertion of such components into the body cavity. In this regard, visibility within a body cavity via such laparoscopic optics and lighting elements may become reduced, deteriorated, or even completely blocked as a result.

Surgical systems, devices, and methods, including those for use in robotic MIS, are described in the present disclosure for addressing one or more problems of known surgical systems, devices, and methods, including those described above and in the present disclosure. It is to be understood that the principles described in the present disclosure can be applied outside of the context of MIS and/or laparoscopic surgery, such as performing scientific experiments and/or procedures in environments that are not readily accessible by humans, including in a vacuum, in outer space, and/or under toxic and/or dangerous conditions, without departing from the teachings of the present disclosure.

The Surgical System (e.g., Surgical Device 100)

An illustration of an example embodiment of a surgical device 100 operable to be inserted into an abdominal cavity of a patient through a single access or opening (such as a single umbilical incision or a natural orifice, hereinafter referred to as an "opening") of the patient and anchored in or about the same opening is depicted in FIG. 1. The surgical device 100 may comprise a port assembly 110, an instrument arm assembly 130, and a camera arm assembly 120.

Figure 2A:
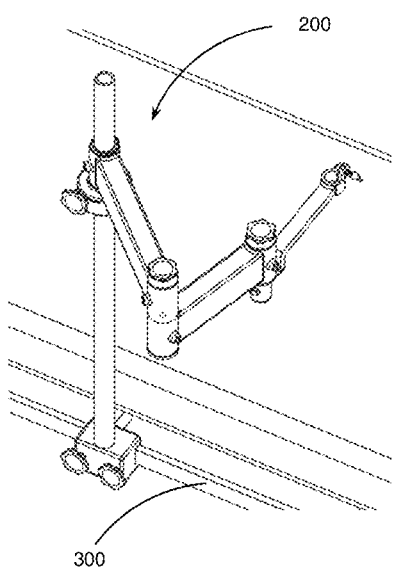
FIG. 2A is illustration of a perspective view of an example embodiment of an external anchor.
Figure 2B:
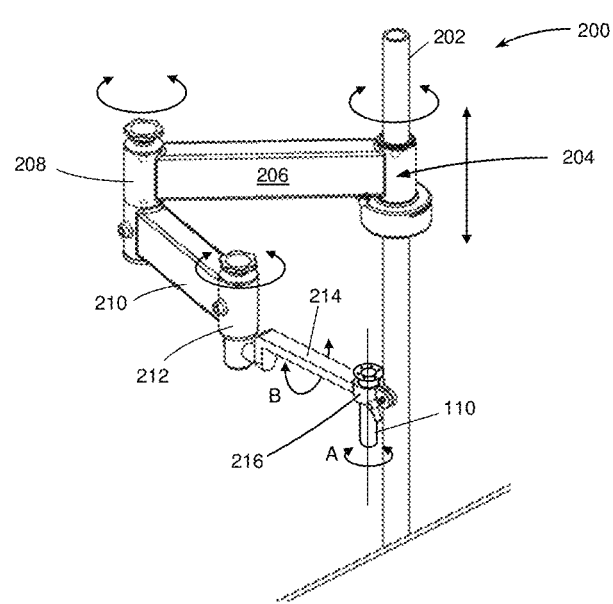
FIG. 2B is another illustration of a perspective view of an example embodiment of an external anchor attached to an example embodiment of a port assembly.
Figure 13:
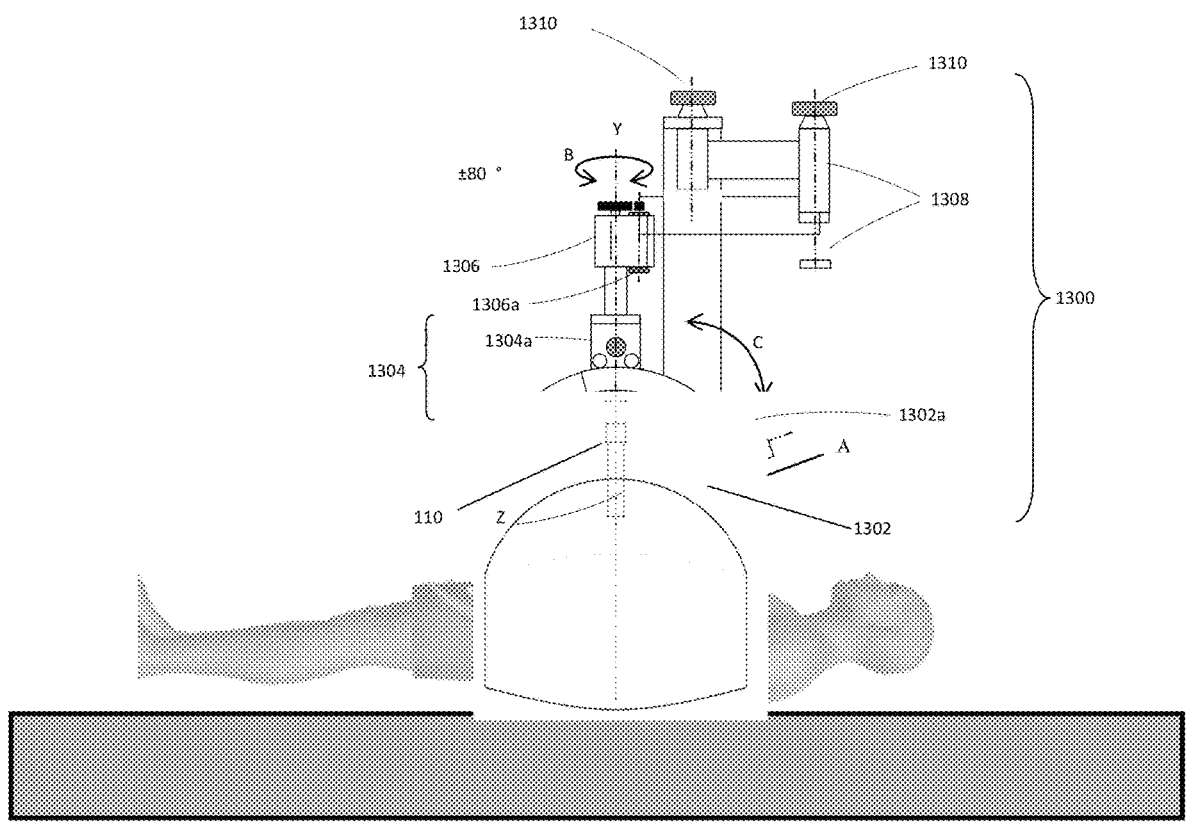
FIG. 13 is an illustration of a perspective view of an example embodiment of an external anchor.

As illustrated in FIGS. 2A and 2B, the surgical device 100 may be provided with an external anchor 200 attachable to the port assembly 110. The external anchor 200 may comprise a configurable assembly of segments 202, 206, 210, and 214 in communication with one another via joints or connecting portions 204, 208, and 212, and external anchor connector 216. The external anchor 200 may be operable to securely fix the position and/or orientation (hereinafter "position") of the port assembly 110 in or about the single opening of the patient, and may also be operable to provide sufficient anchoring and/or reactive forces to stabilize against forces desired and/or necessary to be applied by at least one or more instruments of the surgical device 100, including the instrument arm assembly 130, during a surgical action or procedure. The external anchor 200, including the controllable swivel assembly 1300 (as illustrated in FIG. 13), may also be operable to cooperate with the port assembly 110 to provide one or more in vitro degrees of freedom. In example embodiments, the one or more in vitro degrees of freedom may include a torsional movement, pivotal movement, and/or other movements of the port assembly 110 relative to the external anchor 200. For example, a torsional movement of the port assembly 110, as illustrated by arrow A in FIG. 2B, may allow one or more attached instruments, including an instrument arm assembly 130, to re-position during a surgical procedure (i.e. after set up or installation) so as to access other parts, areas, and/or all quadrants of the abdominal cavity of the patient. As another example, a pivotal movement of the port assembly 110, as illustrated by arrow B in FIG. 2B, may allow the port assembly 110 to be positioned in one of a plurality of angles with respect to opening of the patient, and may also allow attached instruments, including the instrument arm assembly 130, to re-position during a surgical procedure (i.e. after set up or installation) so as to access distal areas of the abdominal cavity of the patient. The other joint portions of the external anchor 200 may also be operable to cooperate and/or assist in desired movements of the port assembly 110. The external anchor 200 may be anchored to one or more stationary objects, such as a side rail 300 of a surgical table/bed illustrated in FIG. 2A. FIG. 13 illustrates other example movements that provide for additional in vitro degrees of freedom via an example embodiment of the controllable swivel assembly 1300. The controllable swivel assembly 1300 will be further described below in the section "(1) Providing the external anchor and installing the outer body of the port assembly (e.g., actions 901 and 902)."

Figure 3A:
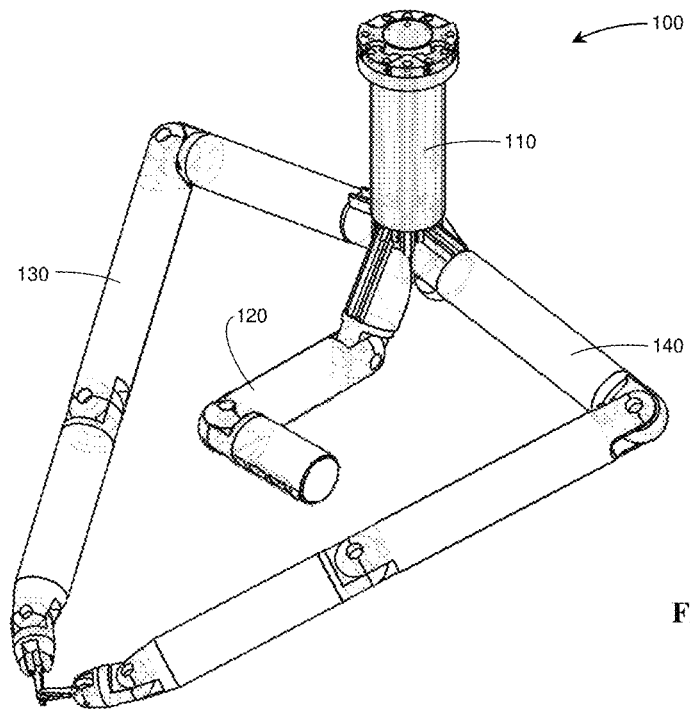
FIG. 3A is an illustration of a perspective view of an example embodiment of a surgical device configured with one port assembly, two instrument arm assemblies, and one camera arm assembly.
Figure 3B:
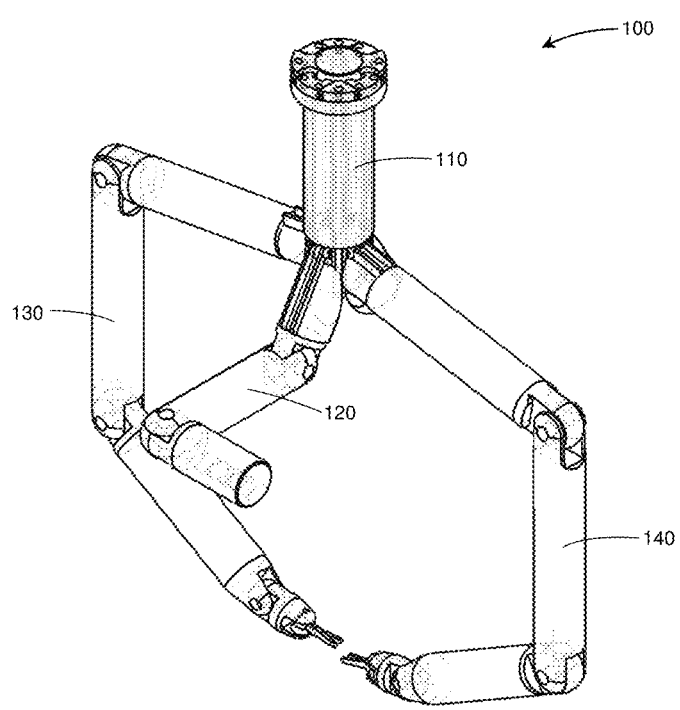
FIG. 3B is another illustration of a perspective view of an example embodiment of a surgical device configured with one port assembly, two instrument arm assemblies, and one camera arm assembly.
Figure 4:
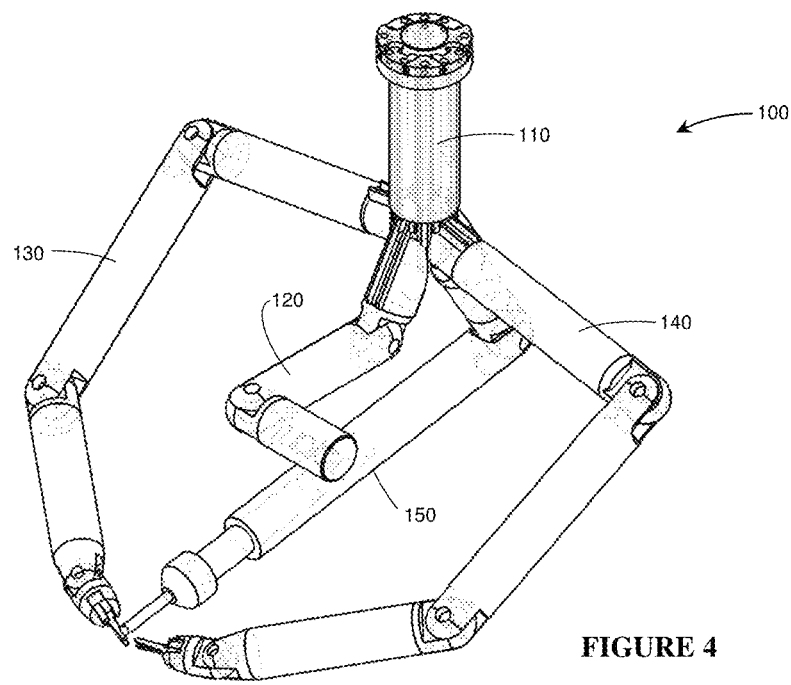
FIG. 4 is an illustration of a perspective view of an example embodiment of a surgical device configured with one port assembly, two instrument arm assemblies, one camera arm assembly, and one instrument arm assembly.
Figure 5:
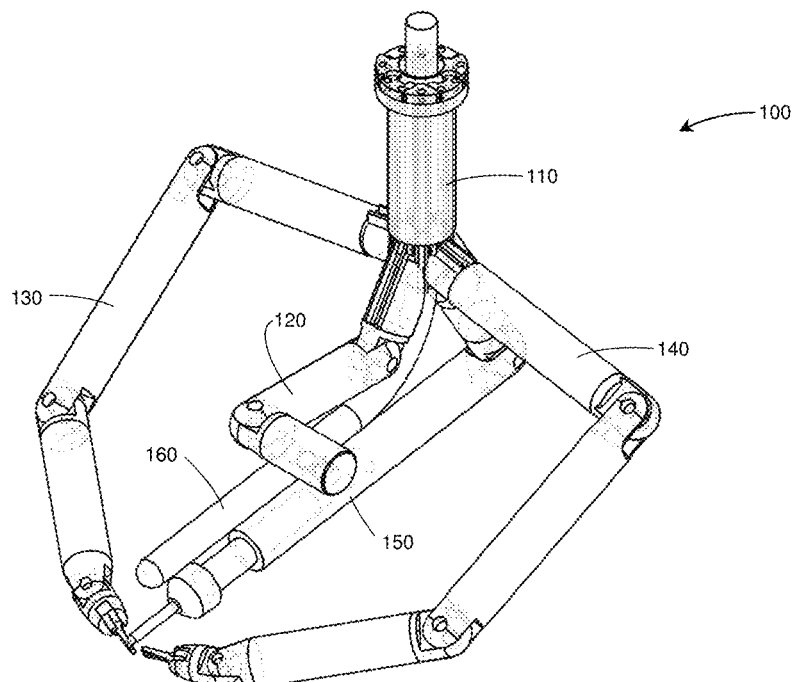
FIG. 5 is an illustration of a perspective view of an example embodiment of a surgical device configured with one port assembly, two instrument arm assemblies, one camera arm assembly, one instrument arm assembly, and one instrument.

The surgical device 100 may further comprise one or more additional instrument arm assemblies, such as second instrument arm assembly 140 illustrated in FIGS. 3A and 3B, attachable to the port assembly 110. One or more of the instrument arm assemblies, including a first instrument arm assembly 130, a second instrument arm assembly 140, a third instrument arm assembly (not shown), a fourth instrument arm assembly (not shown), etc., may be attachable to the port assembly 110 and operable to access and perform one or more surgical actions on any and all parts, areas, and/or quadrants within the abdominal cavity of the patient, including a far or distal end of the cavity, as illustrated in FIG. 3A, and directly below the opening of the patient, as illustrated in FIG. 3B. The surgical device 100 may also comprise one or more additional camera arm assemblies (not shown). The surgical device 100 may further comprise one or more assistant arm assemblies, such as assistant arm assembly 150 illustrated in FIG. 4. Furthermore, the surgical device 100 may comprise another laparoscopic instrument 160, such as a suction instrument, as illustrated in FIG. 5, that can be inserted into the abdominal cavity of the patient before, during, and/or after performing a surgical action or procedure. It is to be understood in the present disclosure that the surgical device 100 may be configurable in a plurality of configurations and arrangements, including having more or less than two instrument arm assemblies (such as third, fourth, fifth, etc. instrument arm assemblies), more than one camera arm assembly (such as second, third, etc. camera arm assemblies), more or less than one assistant arm assembly (such as second, third, etc. assistant arm assemblies), and/or more or less than one laparoscopic tool (such as a second suction tube) in example embodiments without departing from the teachings of the present disclosure.

The Port Assembly (e.g., 110)

Figure 6A:
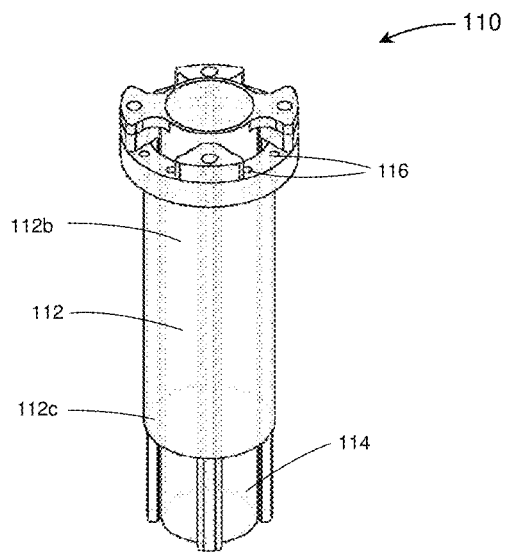
FIG. 6A is an illustration of a perspective view of an example embodiment of a port assembly.
Figure 6C:
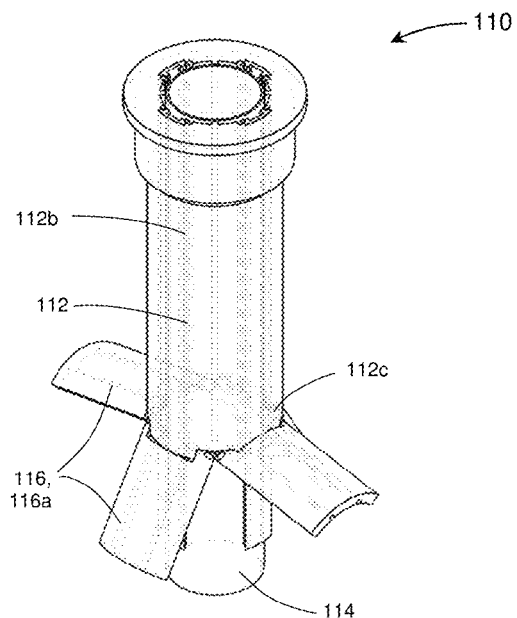
FIG. 6C is an illustration of a perspective view of another example embodiment of a port assembly.
Figure 6B:
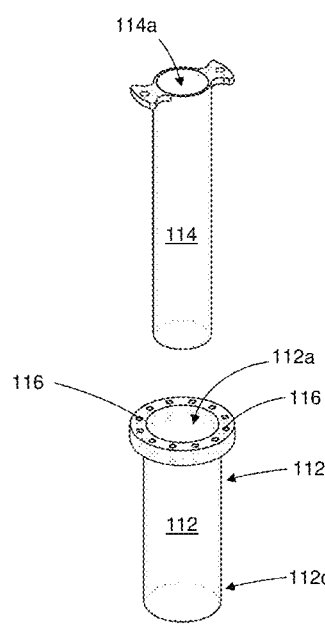
FIG. 6B is another illustration of a perspective view of an example embodiment of a port assembly.
Figure 6E:
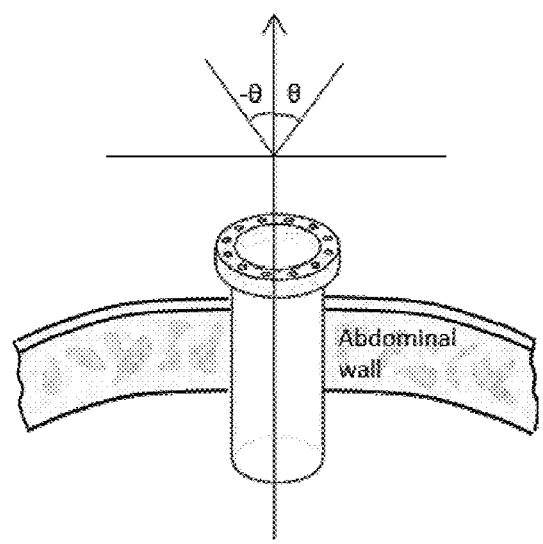
FIG. 6E is an illustration of a perspective view of an example embodiment of a port assembly positionable in one of a plurality of positions (and orientations)

An illustration of an example embodiment of the port assembly 110 is illustrated in FIG. 6A, FIG. 6B, and FIG. 6H, and another illustration of an example embodiment of the port assembly 110 is illustrated in FIG. 6C, FIG. 6D, FIG. 6F, FIG. 6G, and FIG. 6I. The port assembly 110 may be configurable to be inserted in or about a single opening of the patient and fixed in position and/or orientation (hereinafter "position") by at least the external anchor 200. The port assembly 110 may comprise an outer body 112, an inner body 114 configurable to be inserted into and attached to the outer body 112 (as illustrated in FIG. 6A and as further explained below), and one or more anchoring portions 116. The outer body 112 may comprise a first access port 112a operable to receive the inner body 114 (as illustrated in FIG. 6B), a first end 112c insertable in or about the opening of the patient, and a second end 112b attachable to the external anchor connector 216 of the external anchor 200. In an example embodiment, the first end 112c of the outer body 112 may be fixed in position in at least a portion of the opening of the patient and at an angle θ of between about 0 to +/−90 degrees, as illustrated in FIG. 6E.

The port assembly 110 may further comprise an air shutter 114a', as illustrated in FIGS. 6H and 6I. The air shutter 114a' may be any mechanism transitionable between an opened position (which allows access into and out of the second access port 114a (and/or first access port 112a)) and a closed position. The air shutter 114a' may also be transitionable to a partially opened (and/or closed) position in example embodiments. For example, the air shutter 114a' may comprise four quadrant segments, as illustrated in FIGS. 6H and 6I, such as in example embodiments when the air shutter 114a' is provided in a circular or elliptical shape. It is to be understood in the present disclosure that the air shutter 114a' may be provided in other shapes and/or forms, and may comprise other quantities and/or shapes of segments, such as two, three, or more, without departing from the teachings of the present disclosure. It is recognized in the present disclosure that, when an abdominal cavity of a patient is insufflated with gases so as to allow a surgical procedure to be performed, the air shutter 114a' in the closed position may be operable to substantially control or minimize such gases (i.e., seal) from exiting the second access port 114a (and/or the first access port 112a) so as to substantially maintain the insufflation provided in the body cavity. In example embodiments, an air shutter 114a' may be provided on the outer body 112, the inner body 114, or the outer body 112 and the inner body 114.

Prior to the insertion of the inner body 114 into the first access port 112a of the outer body 112 (as illustrated in FIG. 6B), the first access port 112a may be operable to provide an access port (i.e. a passageway) to allow an insertion of one or more instruments, such as one or more instrument arm assemblies, one or more camera arm assemblies, and/or one or more assistant arm assemblies. For example, after the outer body 112 has been inserted and fixed in position in or about the opening of the patient, the first access port 112a may be operable to allow one or more instruments to be inserted and passed through the outer body 112 and into the abdominal cavity of the patient. Before, during, or after the insertion of each instrument into the first access port 112a, the inserted instruments may be attached to the port assembly 110 via one or more of the anchoring portions 116. It is to be understood in the present disclosure that, after the attaching (or anchoring) of an anchoring portion of an inserted instrument (such as 120a, 130a) to one of the anchoring portions 116 of the port assembly 110, the anchoring portion of the already inserted instrument (such as 120a, 130a) may in turn be operable to function as an anchoring portion of the port assembly 110 by enabling an anchoring portion of a subsequent inserted instrument (such as 120a, 130a) to attach (or anchor) to the anchoring portion of the already inserted instrument (such as 120a, 130a). It is recognized in the present disclosure that such a configuration may enable additional arm assemblies, such as camera arm assemblies, instrument arm assemblies, and/or assistant arm assemblies to be inserted, as needed, after the number of anchoring portions 116 of the port assembly 110 has been fully occupied.

After the insertion of the inner body 114 into the first access port 112a of the outer body 112 (as illustrated in FIG. 6A) and the attachment of the inner body 114 to the outer body 112, such as via one or more of the anchoring portions 116 or an anchoring portion of an already inserted instrument (such as 120a, 130a), the first access port 112a may be considered as being replaced by second access port 114a of the inner body 114 in example embodiments. The inner body 114 may be operable to assist with, support, and/or ensure the attachment of inserted instrument(s), including one or more instrument arm assemblies, camera arm assemblies, and/or assistant arm assemblies. The inner body 114 may also be operable to isolate or protect one or more attachment or anchoring portions of the inserted instrument(s), such as the instrument anchoring portion 130a of the instrument arm assembly 130 and/or the camera arm anchoring portion 120a of the camera arm assembly 120. Furthermore, the inner body 114 may be operable to provide an access port (i.e. a passageway) via the second access port 114a so as to allow access to the abdominal cavity of the patient, including allowing the insertion of additional instruments such as instrument 160.

In an example embodiment, the first access port 112a, the second access port 114a, the outer body 112, and/or the inner body 114 may be substantially cylindrical in shape, as illustrated in at least FIGS. 6A-E. The first access port 112a, the second access port 114a, the outer body 112, and/or the inner body 114 may also be formed in any one of a plurality of other shapes, sizes, and/or dimensions without departing from the teachings of the present disclosure.

In an example embodiment, an outer diameter of the outer body 112 (between first end 112c and second end 112b) may between about 21 to 22 mm, an inner diameter of the outer body 112 may be between about 16.5 to 21 mm, an outer diameter of the inner body 114 may be between about 16 to 18 mm, and an inner diameter of the inner body 114 may be between about 15 to 17 mm. In example embodiments, the outer diameter of the outer body 112 (between first end 112c and second end 112b) may be about 22 mm, the inner diameter of the outer body 112 may be about 18 to 19 mm, the outer diameter of the inner body 114 may be about 17.5 to 18 mm, and the inner diameter of the inner body 114 may be about 16.5 to 17 mm. The second end 112b may include a flange portion for, among other things, housing one or more of the anchoring portions 116 and attaching an air shutter 114a' (if provided for the outer body 112) in example embodiments, and the flange portion may have a diameter of about 30-34 mm and a height of about 5 to 10 mm. The overall height of the outer body 112 may be about 80-110 mm and the overall height of the inner body 114 may be about 80-140 mm. It is to be understood in the present disclosure that the above dimensions are merely an illustration of example embodiments, and as such the dimensions may be smaller or larger than those recited above without departing from the teachings of the present disclosure.

The port assembly 110, including the outer body 112, the inner body 114, the surface forming the first access port 112a, the surface forming the second access port 114a, and/or the anchoring portion 116, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. The air shutter 114a' for the inner body 114 and/or outer body 112 may be formed using any one or more of a plurality of materials, such as bio-compatible materials (such as silicone rubber and polyurethane). It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

In example embodiments, such as those illustrated in FIGS. 6C, 6D, 6F, 6G, and 6I, the port assembly 110 may further comprise one or more flap sections 116a, or the like. The flaps 116a may provide or assist in providing similar or substantially the same functionality as the anchoring portion 116 described above, including the anchoring functionality of the anchoring portion 116 in example embodiments. Specifically, the one or more flaps 116a may be operable to provide or assist in providing anchoring (or securing or locking) of one or more arm assemblies, such as a camera arm assembly, instrument arm assembly, and/or assistant arm assembly, to the port assembly 110. Although the example embodiments in FIGS. 6C, 6D, 6F, 6G, and 6I illustrate a port assembly 110 comprising four flaps 116a, it is to be understood in the present disclosure that the port assembly 110 may comprise other quantities, shapes, and/or forms of flaps without departing from the teachings of the present disclosure. For example, the port assembly 110 may comprise less than or more than four flaps in example embodiments.

Figure 6D:
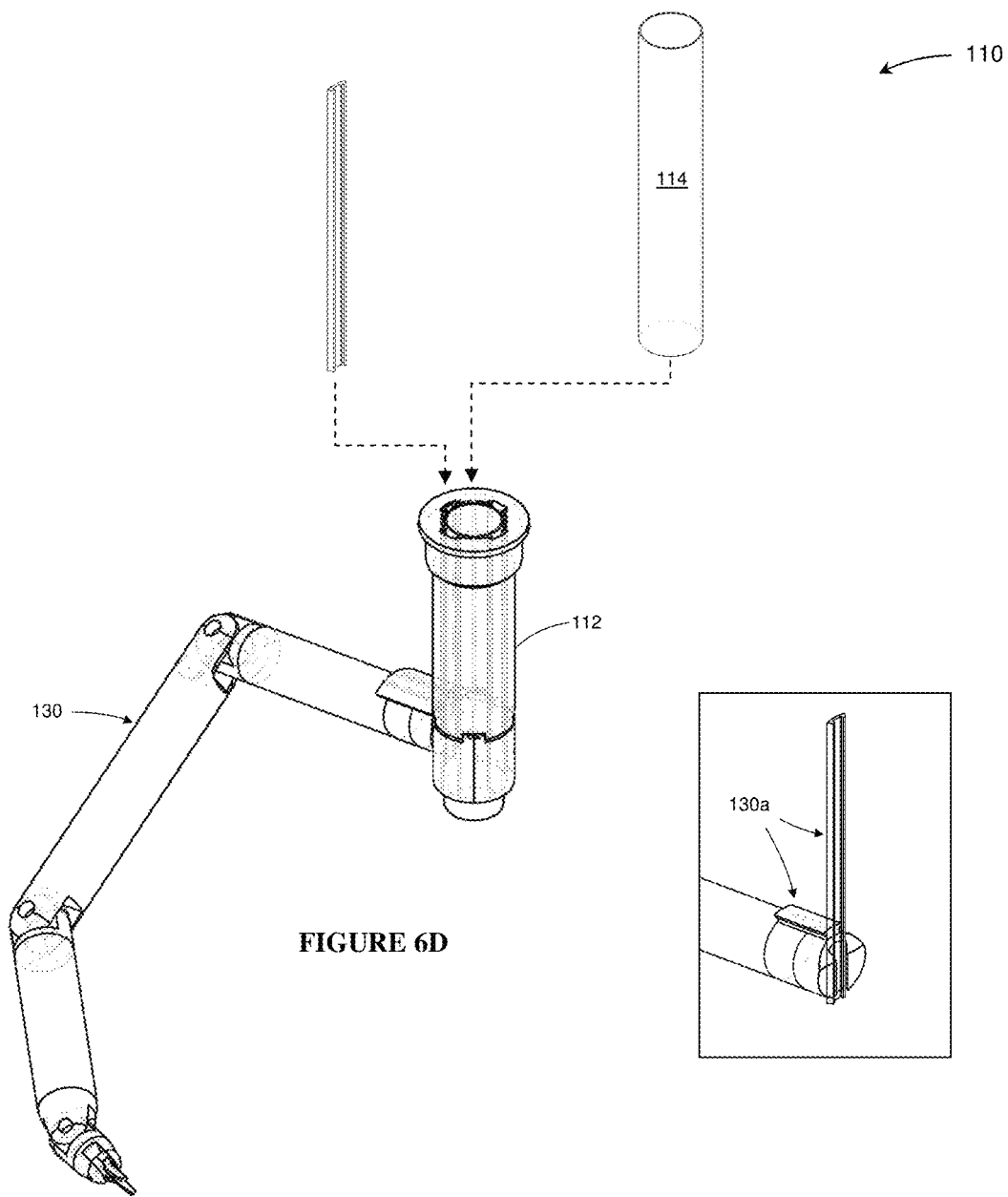
FIG. 6D is another illustration of a perspective view of an example embodiment of a port assembly.
Figure 6F:
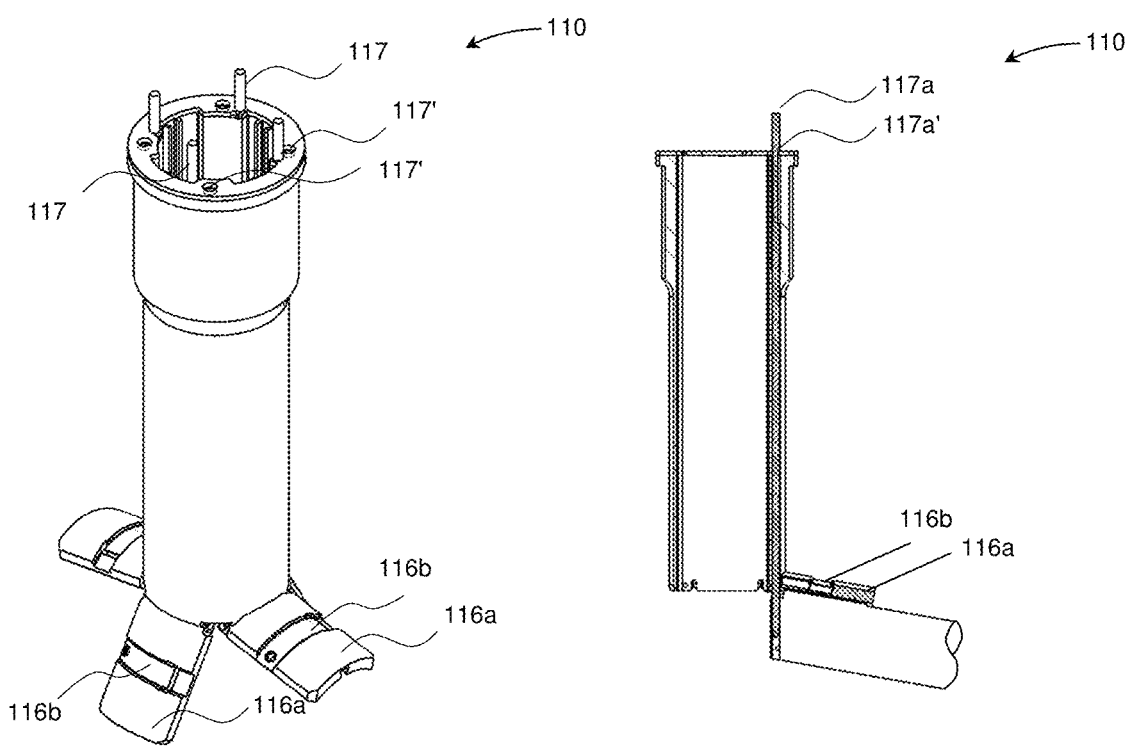
FIG. 6F is an illustration of a perspective view and a cross sectional view of an example embodiment of a port assembly in an engaged position and having flaps, receiving sections for receiving securing pins, and spring locks provided on each flap.
Figure 6G:
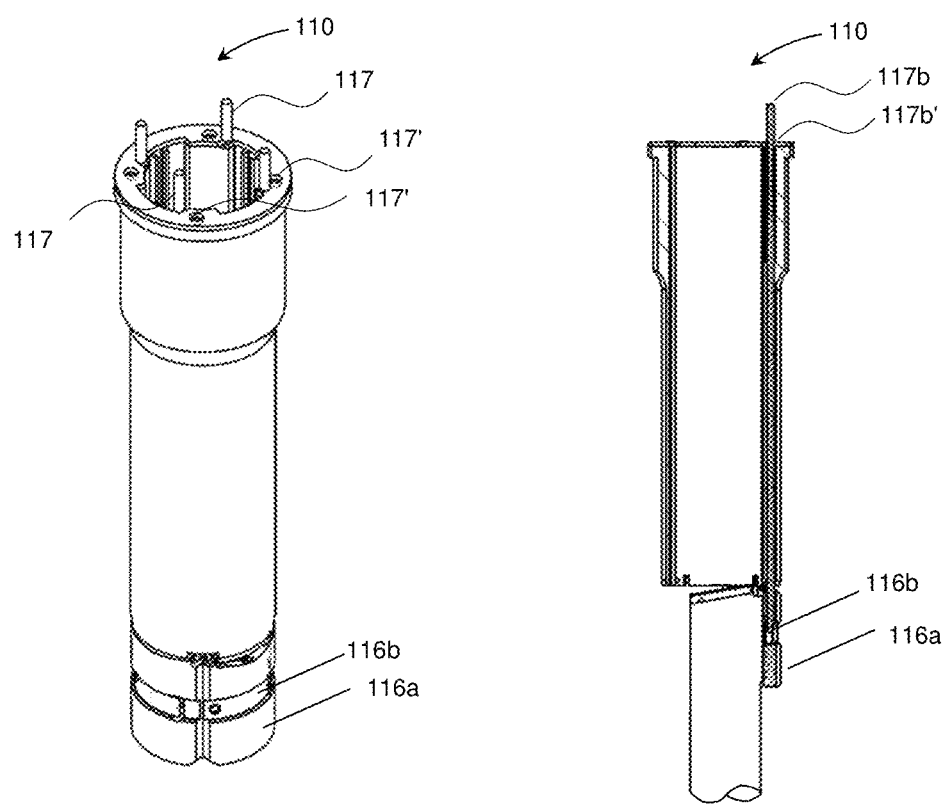
FIG. 6G is another illustration of a perspective view and a cross sectional view of an example embodiment of a port assembly in a transitionable position and having flaps, receiving sections for receiving securing pins, and spring locks provided on each flap.

The one or more flaps 116a of the port assembly 110 may be further operable to transition between an engaged position (which may be a position wherein an arm assembly secured to the flap 116a is ready to perform a surgical procedure, and wherein such position provides a clear passageway of the port assembly 110 for other arm assemblies to be inserted through the port assembly 110 and into the body cavity) and a transitionable position (which may be a position wherein an arm assembly secured to the flap 116a is ready to be removed from or inserted into the body cavity and port assembly 110). Example embodiments of a flap 116a in an engaged position and a transitionable position are illustrated in FIGS. 6F and 6G, respectively. Supporting pins 117 may be provided for securing the one or more flaps 116a of the port assembly 110 in the engaged position and/or transitionable position.

Figure 6L:
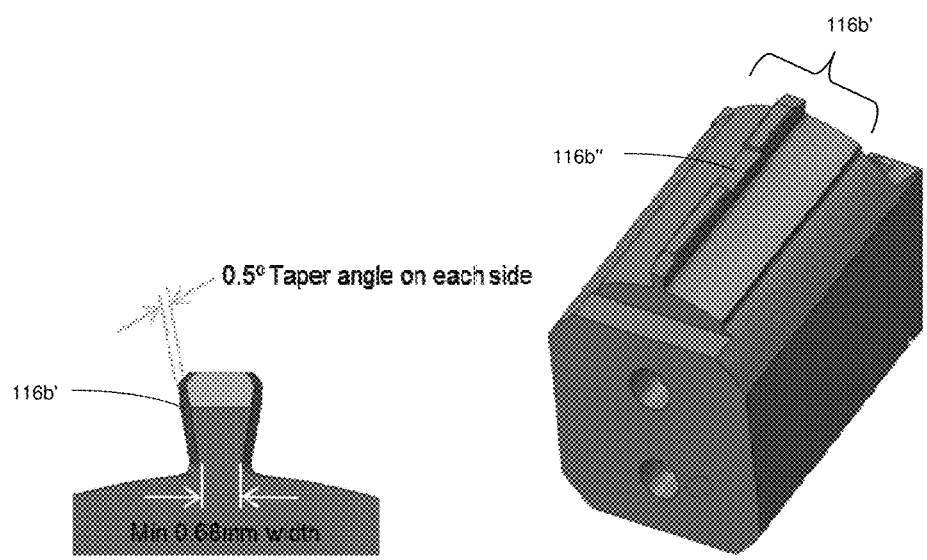
FIG. 6L is an illustration of a cross sectional view and perspective view of a spring lock engaging portion of an arm assembly for use in engaging a corresponding spring lock.

An example embodiment of the flap 116a may further comprise a spring lock 116b, as illustrated in FIG. 6F, FIG. 6G, FIG. 6J, and FIG. 6K, which may be in the form of a spring plate, or the like. The spring lock 116b may be operable to secure or lock an arm assembly, such as a camera arm assembly, instrument arm assembly, and/or assistant arm assembly, to the flap 116a when engaged in the locked position. In example embodiments, as illustrated in FIG. 6L, each arm assembly may comprise a corresponding spring lock engaging portion 116b' having a corresponding spring lock receiving portion 116b", or the like, for receiving the spring lock 116b of the flap 116a. For example, if the arm assembly is an instrument arm assembly 130, then the instrument arm assembly 130 (and/or the instrument anchoring portion 130a of the instrument arm assembly 130) may comprise a corresponding spring lock engaging portion 116b' having a spring lock receiving portion 116b". Similarly, if the arm assembly is a camera arm assembly 120, then the camera arm assembly 120 (and/or the camera anchoring portion 120a of the camera arm assembly 120) may comprise a corresponding spring lock engaging portion 116b' having a spring lock receiving portion 116b".

To engage in a locked position, a spring lock engaging portion 116b' of an arm assembly (an example portion of which is illustrated in FIG. 6L) may be inserted into a corresponding receiving portion of a flap 116a. This is illustrated in FIG. 6K, wherein the spring lock 116b has not yet secured or locked the arm assembly to the flap 116a. The arm assembly will be secured or locked to the flap 116a, as illustrated in FIG. 6J when the arm assembly is further inserted until the spring lock 116b is received by the spring lock receiving portion 116b" of the arm assembly.

An arm assembly secured or locked to the flap 116a in the manner described above (FIG. 6J) may be unsecured or unlocked by unlocking the spring lock 116b from the spring lock receiving portion 116b" of the arm assembly. For example, a supporting pin 117, or the like, may be provided to push, displace, or unlock at least a portion of the spring lock 116b in such a way that the spring lock 116b is no longer received by the spring lock receiving portion 116b" of the arm assembly.

The Camera Arm Assembly (e.g., 120)

Figure 8A:
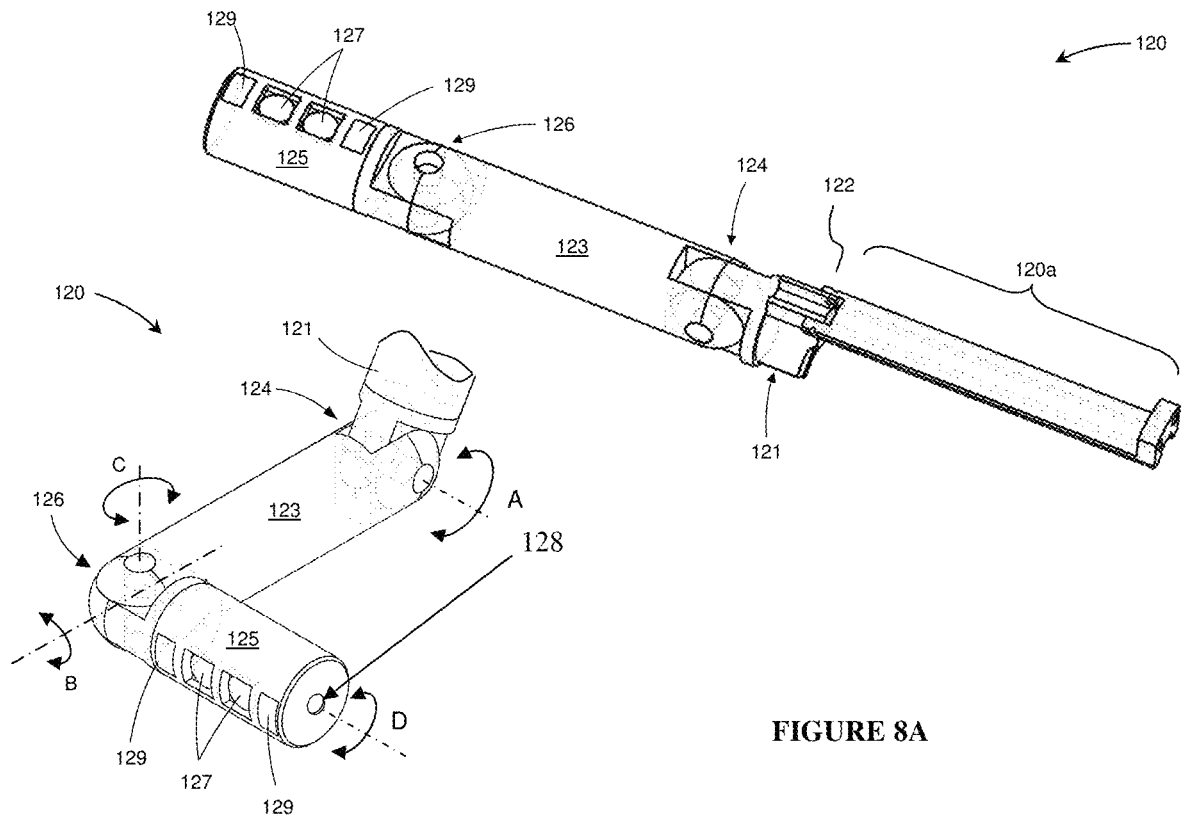
FIG. 8A is an illustration of two perspective views of an example embodiment of a camera arm assembly.
Figure 12:
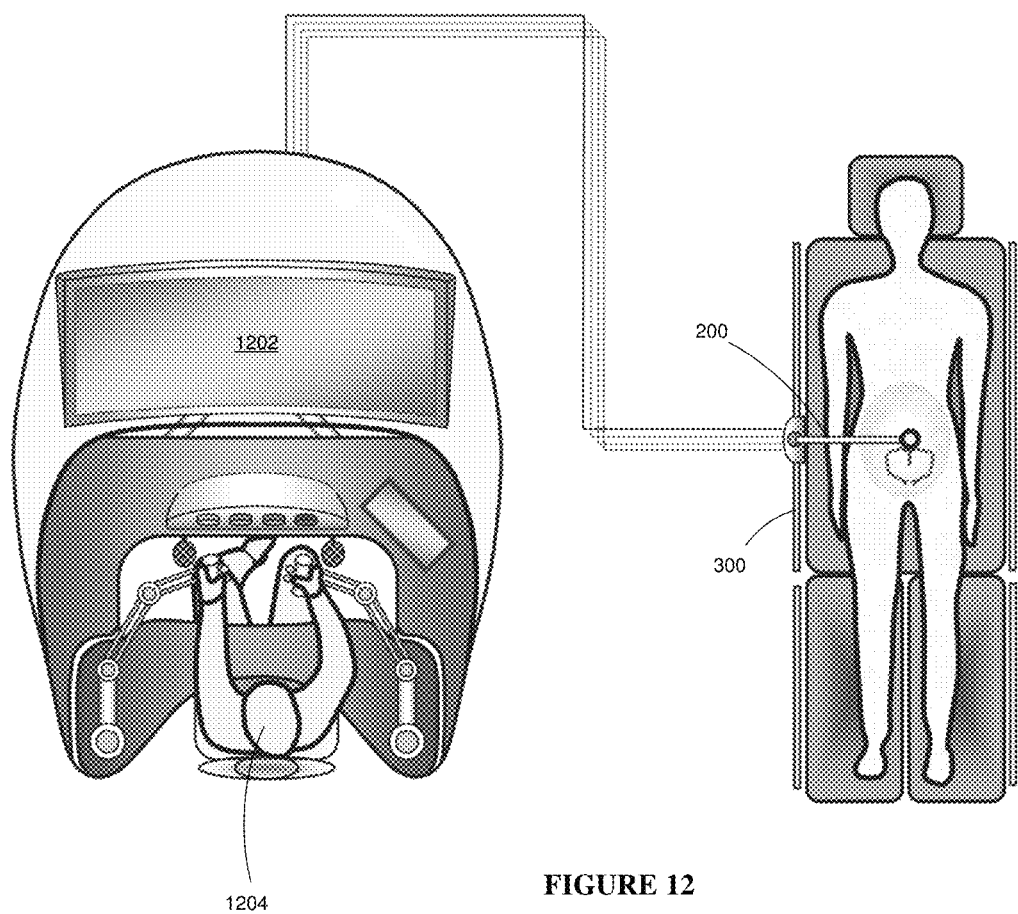
FIG. 12 is an illustration of a perspective view of an example embodiment of a surgical device system.

In an example embodiment, the surgical device 100 may comprise one or more camera arm assemblies, such as camera arm assembly 120, configurable to attach to the port assembly 110. One or more of the camera arm assemblies may comprise a configurable serial (or linear) arrangement of a plurality of camera arm segments, camera joint portions, and at least one camera integrated into and/or attached to one or more of the camera arm segments and/or camera joint portions. As illustrated in FIG. 8A, the camera 127 may be a standard and/or high definition 2-dimensional (2D) and/or 3-dimensional (3D) camera operable to capture imaging, such as 2D and/or stereoscopic and/or autostereoscopic 3D imaging, including images, video, and/or audio, and provide in real-time via wired and/or wireless communication the captured imaging, including images, video, and/or audio, to a computing device (or system) of one or more nearby and/or remotely located surgical teams 1204. The computing device (or system) may comprise one or more processors, one or more computer-human interfaces, one or more graphical displays (such as computer screens, television screens, portable devices, wearable devices such as glasses, etc.), and/or other devices and/or systems, an example of which is illustrated in FIG. 12. The one or more nearby and/or remotely located surgical teams 1204 may be operable to view, hear, sense, analyze, and control (such as pan, zoom, process, adapt, mark, change resolution, etc.) the imaging displayed or represented on one or more standard and/or high definition 2D and/or 3D graphical displays 1202, such as shown in the illustration of FIG. 12, and/or portable and/or wearable devices adapted to receive 2D and/or 3D imaging (not shown). One or more of the camera arm assemblies may also comprise one or more illumination sources 129, such as an LED, or the like, operable to illuminate or sense at least one or more parts, sections, and/or quadrants of the abdominal cavity of the patient, including instruments provided in the abdominal cavity of the patient. One or more of the camera arm assemblies 120 may further comprise one or more internal temperature control assemblies operable to control (such as reduce) the temperature of one or more components of the camera arm assembly 120.

Figure 8B:
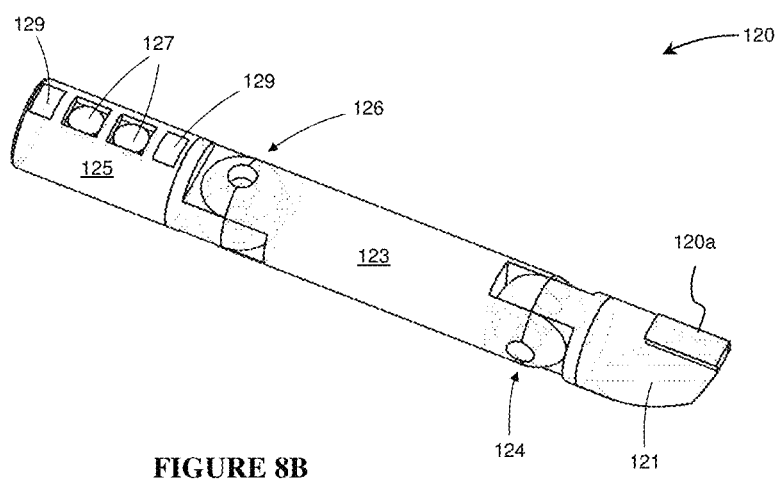
FIG. 8B is an illustration of a perspective view of another example embodiment of a camera arm assembly.

As illustrated in the example embodiment of FIGS. 8A and 8B, one or more of the camera arm assemblies 120 may comprise a first camera arm segment 121, a second camera arm segment 123, and a third camera arm segment 125. One or more of the camera arm assemblies 120 may also comprise corresponding camera joint portions, such as first camera joint portion 124 and second camera joint portion 126. Each camera joint portion may be configurable, either manually and/or via the computing device (or system), to provide an attached camera arm segment with one or more in vivo degrees of freedom when the camera arm assembly 120 is provided in the abdominal cavity of the patient. For example, the first camera joint portion 124 may be operable to provide the second camera arm segment 123 with a pivotal movement relative to the first camera joint portion 124, as illustrated by arrow A in FIG. 8A, and/or a torsional movement relative to the first camera joint portion 124, as illustrated by arrow B in FIG. 8A. As another example, the second camera joint portion 126 may be operable to provide the third camera arm 125 with a pivotal movement relative to the second camera joint portion 126, as illustrated by arrow C in FIG. 8A, and/or a torsional movement relative to the second camera joint portion 126, as illustrated by arrow D in FIG. 8A. Accordingly, one or more of the camera arm assemblies 120 may be configurable, either manually and/or via the computing device (or system), to provide multiple in vivo degrees of freedom and, together with the at least one in vitro degree of freedom provided by the port assembly 110, including the controllable swivel assembly 1300 (see FIG. 13), the one or more of the camera arm assemblies may be configurable to provide multiple degrees of freedom.

Each camera joint portion may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each camera arm assembly may also comprise one or more internal motors (not shown), or the like, operable to actuate the gears of each camera joint portion and/or the camera arm segments. In this regard, each of the above mentioned motors, camera joint portions, and/or camera arm segments may be operable to communicate from and/or to the computing device (or system) of one or more nearby and/or remotely located surgical teams 1204 via wired and/or wireless communication in example embodiments. Furthermore, each of the abovementioned motors, camera joint portions, and/or camera arm segments may be operable to receive power from an external power source and/or the computing device (or system) via wired and/or wireless transmissions in example embodiments.

One or more internal temperature control assemblies (not shown) may be provided for each camera arm assembly 120. Each internal temperature control assembly may be operable to control (such as reduce) the temperature and/or heat emission of the aforementioned camera(s) 127, illumination source(s) 129, gears and/or gear assemblies, motors, camera joint portions (such as 124 and 126), and/or camera arm segments (such as 121, 123, and 125). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well as any solids (if used), may be provided through an interior of the camera arm assembly 120 without increasing dimensions (such as diameter) of the camera arm assembly 120.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the abdominal cavity, such as via opening 128 in FIG. 8A, during a surgical procedure.

When the internal temperature control assembly utilizes liquids, or the like, example embodiments may be operable to discharge or recycle such liquids outside of the body cavity.

When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the camera arm assembly 120.

In example embodiments, the internal temperature control assembly may utilize a combination of gases, liquids, solids, and/or the like without departing from the teachings of the present disclosure.

The camera arm assembly 120 may also comprise a camera anchoring portion 120a operable to attach (or secure) the camera arm assembly 120 to one or more anchoring portions 116 (and/or flaps 116a), and this may be provided via the first camera arm segment 121. FIG. 8A illustrates an example embodiment of a camera anchoring portion 120a operable to attach to the anchoring portion 116 of the example embodiment of the port assembly in FIG. 6A, and FIG. 8B illustrates an example embodiment of a camera anchoring portion 120a operable to attach to the flaps 116a of the example embodiment of the port assembly in FIG. 6C.

These and other types or configurations of camera anchoring portions 120a and anchoring portions 116 (and/or flaps 116a) may be provided and configured in example embodiments without departing from the teachings of the present disclosure.

In an example embodiment, the camera arm segments, including the first camera arm segment 121, the second camera arm segment 123, and/or the third camera arm segment 125, may be substantially cylindrical in shape, as illustrated in at least FIGS. 8A and 8B. The camera arm segments, including the first camera arm segment 121, the second camera arm segment 123, and/or the third camera arm segment 125, may also be formed in any one of a plurality of other shapes, sizes, and/or dimensions without departing from the teachings of the present disclosure.

In an example embodiment, the camera anchoring portion 120a may be attachable to the rest of the camera arm assembly 120, such as via the first camera arm segment 121, via hinge joint 122, or the like, and the camera arm anchoring portion 120a may be of sufficient length and thickness, such as 80 to 130 mm in length and about 1 to 2 mm in thickness, to attach to one or more anchoring portions 116 and/or flaps 116a.

After the camera arm assembly 120 is inserted through the port assembly 110 and into a body cavity of a patient, the camera anchoring portion 120a may be securely received by the port assembly 110 via anchoring portions 116 and/or flaps 116a. To enable the insertion (and removal) of other instruments, such as one or more instrument arm assemblies 130, the camera arm assembly 120 may be positionable in such a way that a clear path (via the first access port 112a and/or second access port 114a of the port assembly 110) may be provided to allow the insertion (and removal) of other instruments (see, for example, FIG. 10D). Such positioning may be secured by the use of one or more supporting pins 117, or the like. The supporting pins 117 may be provided in the form of curved plates, as illustrated in FIG. 6D and FIG. 10D, or other shapes and forms. In example embodiments, such supporting pins 117 may also be operable to provide a separation or isolation of any cables and tubes (not shown) from the opening portion of the first access port 112a and/or second access port 114a of the port assembly 110.

In example embodiments, the supporting pins 117 may be provided so as to not only secure the position of the camera arm assembly 120 in such a way as to allow insertion (and removal) of other instruments, but to also secure the position of the camera arm assembly 120 so as to allow removal (and insertion) of the camera arm assembly 120 itself. For example, as illustrated in FIG. 6F and FIG. 6G, the port assembly 110 may comprise a plurality of receiving sections 117' for support pins 117. One of the receiving portions 117a' may be operable to receive a support pin 117a to securely position one of the flaps 116a of the port assembly 110 (and thus securely position an arm assembly, such as a camera arm assembly, instrument arm assembly, or an assistant arm assembly) in an engaged position, as illustrated in the second illustration of FIG. 6F. To securely position the flap 116a of the port assembly 110 (and thus vertically position an arm assembly, such as a camera arm assembly, instrument arm assembly, or assistant arm assembly) in a transitionable position, as illustrated in the second illustration of FIG. 6G, a support pin 117b may be provided in receiving portion 117b'.

Figure 8C:
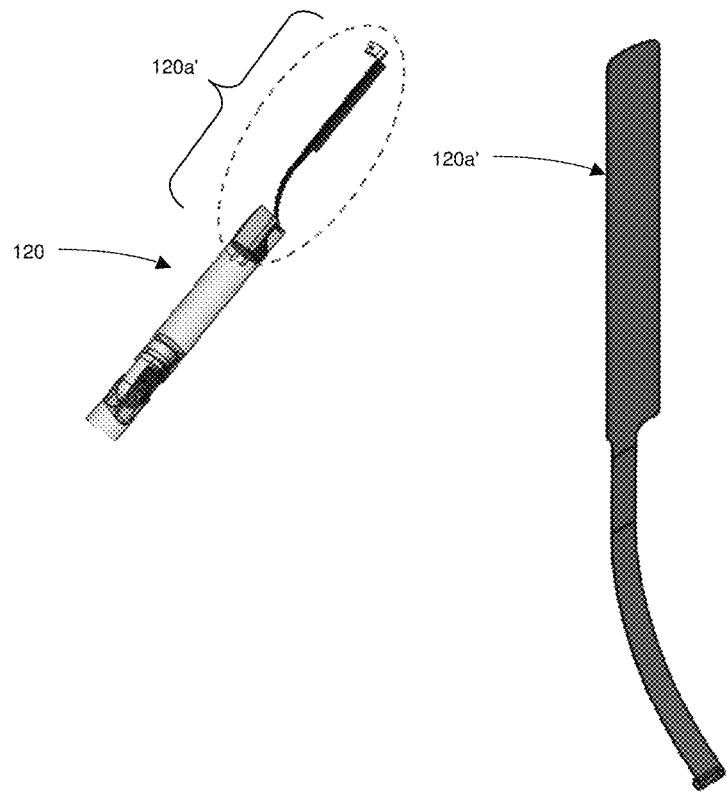
FIG. 8C is an illustration of a perspective view of an example embodiment of a camera arm assembly with a camera anchoring portion and a camera anchoring portion only.
Figure 8D:
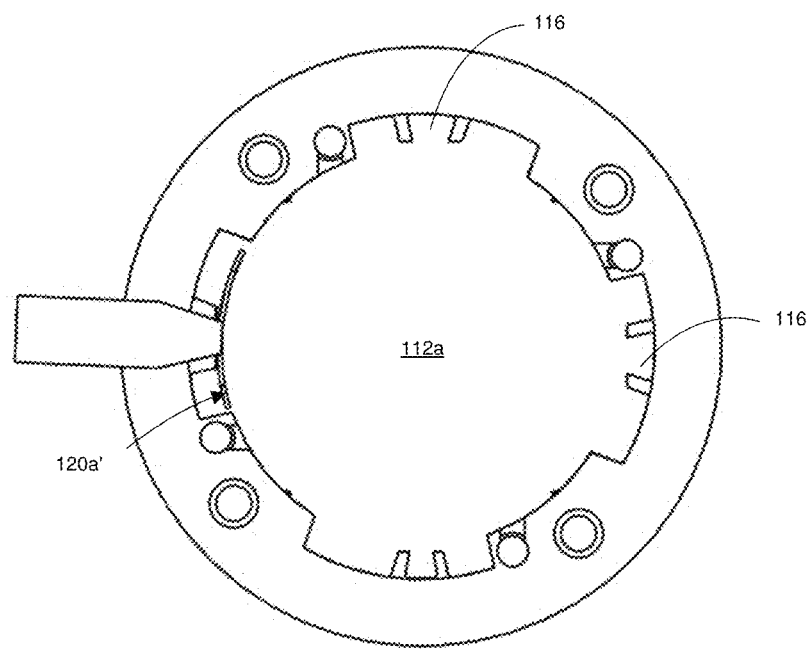
FIG. 8D is an illustration of a top view of an example embodiment of a camera anchoring portion of a camera arm assembly anchored to an interior of a port assembly, along with cabling provided between the camera anchoring portion and the port assembly.
Figure 8E:
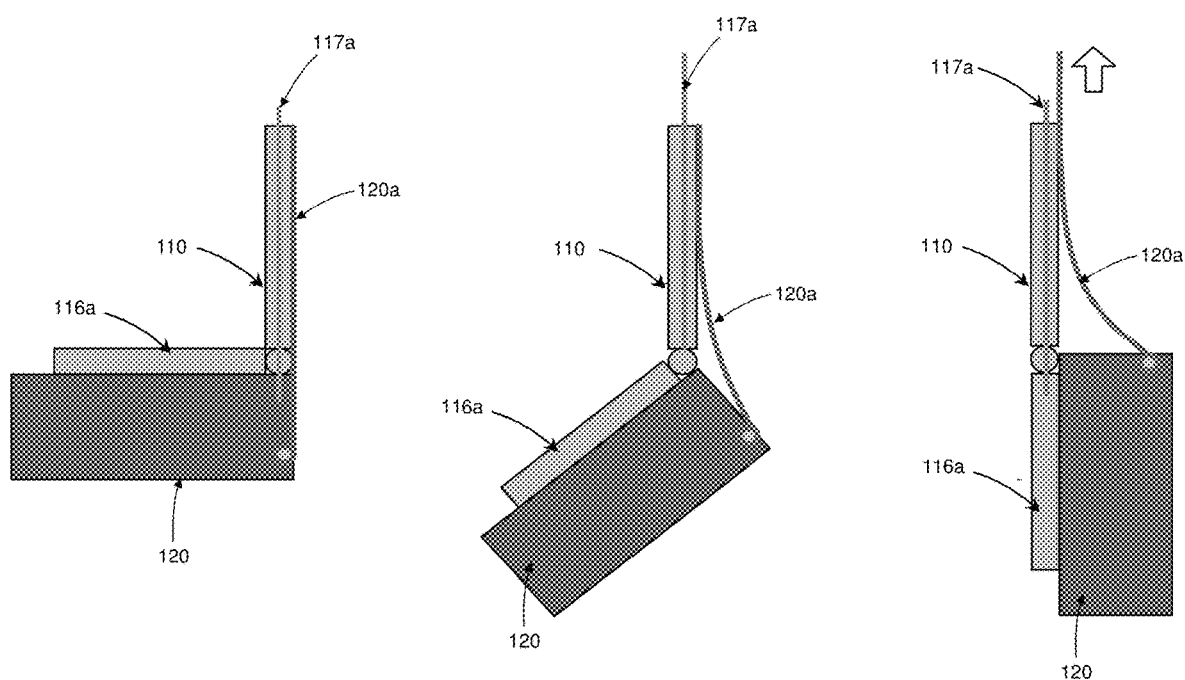
FIG. 8E is an illustration of a perspective view of an example embodiment of a camera arm assembly positioned in an engaged position, a camera arm assembly being transitioned, and a camera arm assembly positioned in a transitionable position.

Example embodiments of the camera anchoring portion 120a', such as those illustrated in FIGS. 8C-E, may comprise at least a restorative portion 120a", or the like, which may be a portion of the camera anchoring portion 120a' that is slightly curved in shape when in its natural shape/position (see, for example, FIG. 8C). The restorative portion 120a" may provide a restoring force, such as a spring-like elastic force, when the restorative portion 120a" of the camera anchoring portion 120a' is deviated from its natural shape/position. For example, if an external force is applied to the restorative portion 120a" of the camera anchoring portion 120a' so as to result in the overall shape of the camera anchoring portion 120a' deviating from its natural shape/position (such as being brought to a substantially straight shape), and the external force is then removed, the restoring force of the restorative portion 120a" of the camera anchoring portion 120a' may be operable to cause the camera anchoring portion 120a' to return to its natural shape/position, as illustrated in FIG. 8C. It is recognized in the present disclosure that such an embodiment of the camera anchoring portion 120a' may enable a safe and effective insertion and/or removal of the camera arm assembly 120 into and/or from the body cavity of a patient. For example, as illustrated in the sequence of illustrations of FIG. 8E, a camera arm assembly 120 securely positioned in an engaged position via supporting pins 117a (left illustration of FIG. 8E) may be changed to be in a transitionable position by removing the support pins 117a (middle illustration of FIG. 8E), which enables the restoring forces of the restorative portion 120a" of the camera anchoring portion 120a' to return the camera anchoring portion 120a' to its natural shape/position and position the camera arm assembly 120 for removal or insertion (right illustration of FIG. 8E).

In an example embodiment, the length of the first camera arm segment 121 may be between about 5 to 35 mm, the length of the second camera arm segment 123 may be between about 50 to 70 mm, the length of the third camera arm segment 125 may be between about 16 to 45 mm, and the overall length of the collective camera arm segments and camera joint portions may be between about 110 to 150 mm. In example embodiments, the length of the first camera arm segment 121 may be between about 10 to 20 mm, the length of the second camera arm segment 123 may be between about 56 to 60 mm, the length of the third camera arm segment 125 may be between about 34 to 40 mm, and the overall length of the collective camera arm segments and camera joint portions may be between about 120 to 140 mm. In example embodiments, a length of one or more of the camera arm segments may also be adjustable by the surgical team 1204 before, during, and/or after insertion of the camera arm assembly into the cavity of the patient. The outer diameter of one or more of the camera arm segments may be about 10 to 16 mm. In an example embodiment, the outer diameter of one or more of the camera arm segments may be about 16 mm. It is to be understood in the present disclosure that the above dimensions are merely an illustration of example embodiments, and as such the dimensions may be smaller or larger than those recited above without departing from the teachings of the present disclosure.

The camera arm assembly 120, including the first camera arm segment 121, the second camera arm segment 123, the third camera arm segment 125, the first camera joint portion 124, the second camera joint portion 126, the camera arm anchoring portion 120a, and/or the hinge joint 122, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure. It is to be understood in the present disclosure that the above materials are merely an illustration of example embodiments, and these and other materials and compositions may be used without departing from the teachings of the present disclosure.

Figure 8F:
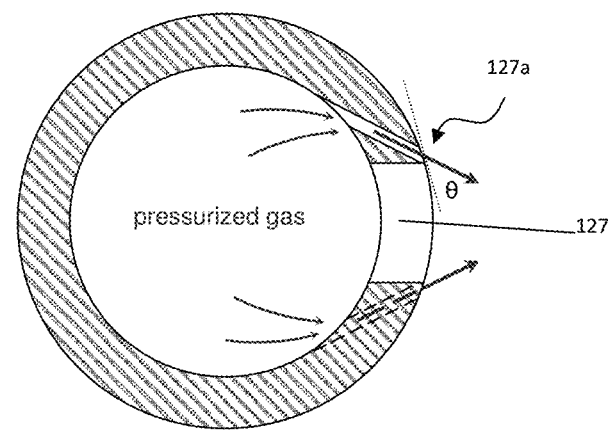
FIG. 8F is an illustration of a cross sectional view of a camera arm assembly having an internal temperature control assembly.
Figure 8G:
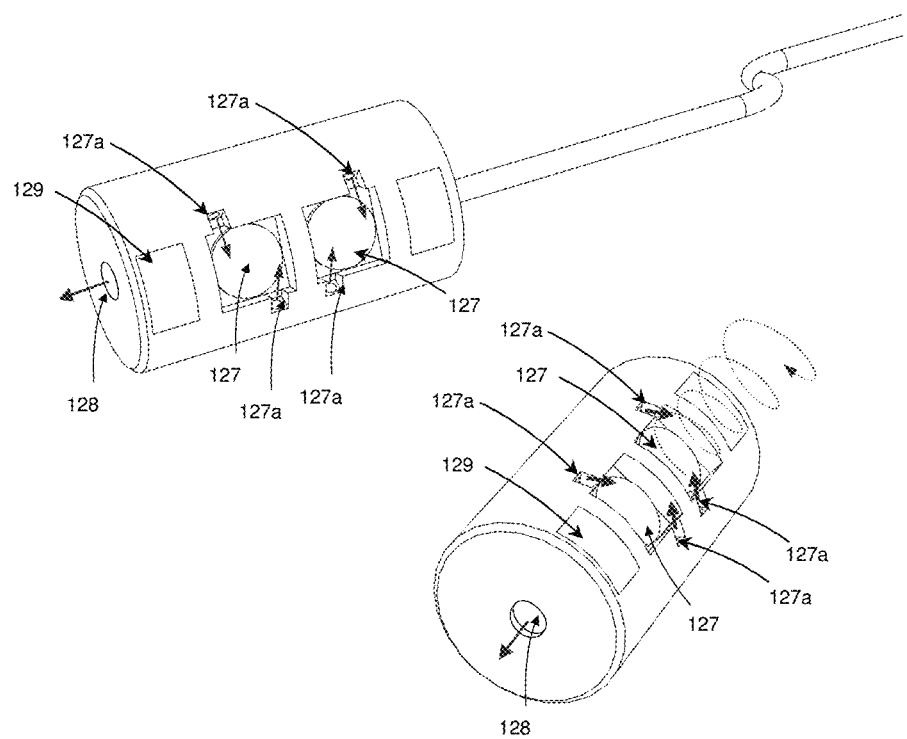
FIG. 8G is an illustration of perspective views of a camera arm assembly having internal temperature control assemblies.

As illustrated in FIGS. 8E-G, the camera arm assembly 120 may further comprise a gas shield 127a located nearby a lens of the camera 127. The camera arm assembly 120 may further comprise a gas shield (not shown) located nearby an illumination source 129 and/or any other sensors provided by the camera arm assembly 120. The gas shield 127a may comprise one or more openings or the like, one or more external gas sources (not shown), and one or more tubes, channels, or the like, between the one or more external gas sources and the one or more openings of the gas shield 127a.

In operation, the gas shield 127a may be operable to provide pressurized gases (and/or liquids), such as carbon dioxide, oxygen, other gases or liquids, or combinations thereof, via the one or more openings of the gas shield 127a to an area in front of the camera 127 (as well as the illumination sources 129 and/or other sensors). In example embodiments, the pressurized gases (and/or liquids) may be discharged from the one or more openings of the gas shield 127a at an angle $\theta_2$, wherein $\theta_2$ is an angle between about 0 and 90 degrees, as illustrated in FIG. 8F. In example embodiments, the angle $\theta_2$ and/or certain characteristics (such as flow, pressure, temperature, and/or composition) of the discharged pressurized gases (and/or liquids) may be controlled and/or changed on demand, continuously, and/or intermittently.

As illustrated in FIG. 8G, the discharged pressurized gases from two or more example embodiments of the gas shields 127a (corresponding to one camera 127) may be operable to cooperate together (or disturb each other) so as to form a spiral-like gas flow, a radially inward and/or outward gas flow, and/or the like, in front of the camera 127 so as to form an effective gas barrier in front of the camera 127.

Although FIGS. 8E and 8G depict two openings of the gas shield 127a for each camera 127, it is to be understood in the present disclosure that example embodiments may also comprise a single opening of the gas shield 127a (not shown) or more than two openings of the gas shield (not shown) for each camera 127 without departing from the teachings of the present disclosure.

It is recognized in the present disclosure that example embodiments of the gas shield 127a may be operable to prevent, minimize, or substantially eliminate an occurrence of contamination and/or partial or complete blockage of the camera 127 (and/or the illumination sources 129 and/or other sensors) during a surgical procedure due to fogging, tissue debris, liquids (such as blood), and/or particle accumulation. In this regard, example embodiments of the gas shield 127a may be operable to maintain substantial visibility within a body cavity via such cameras 127 (and illumination sources 129 and/or other sensors) and effectively enable surgical teams viewing images, video, and/or other information captured by such cameras 127 (and illumination sources 129 and/or other sensors) to carry on performing surgical procedures without interruption.

Each opening of the gas shield 127a may be in any shape and form. For example, the opening may be a circular opening (as shown in FIGS. 8E-G), an elliptical opening, a square opening, a rectangular opening, a triangular opening, or other geometrical shapes, and/or combinations thereof.

Each opening of the gas shield 127a may have a diameter of about 0.3 mm or less for circular or elliptical openings.

The Instrument Arm Assembly (e.g., 130, 140)

In an example embodiment, the surgical device 100 may comprise one or more instrument arm assemblies, such as the first instrument arm assembly 130, a second instrument arm assembly 140, a third instrument arm assembly (not shown), a fourth instrument arm assembly (not shown), etc., each configurable to attach to the port assembly 110. One or more of the instrument arm assemblies (such as 130, 140) may comprise a configurable serial (or linear) arrangement of a plurality of instrument arm segments and joint portions, and at least one end instrument 139, including instruments 139a and 139b, integrated into and/or connected to one or more of the instrument arm segments and/or joint portions. The end instrument 139 may be any instrument suitable for use in MIS procedures, such as a cutting and/or gripping instrument. One or more of the instrument arm assemblies (such as 130, 140) may also comprise one or more illumination sources (not shown), such as an LED, or the like, operable to illuminate one or more parts of the end instrument 139, including instruments 139a and 139b, and/or instrument arm assemblies and/or parts, sections, and/or quadrants of the abdominal cavity of the patient. One or more of the instrument arm assemblies (such as 130, 140) may also comprise a haptic and/or force feedback instrument (not shown) and/or other sensors and/or instruments operable to provide to the computing device of one or more nearby and/or remotely located surgical team 1204 one or more of a plurality of feedback responses and/or measurements, including those pertaining to position (including orientation), applied force, proximity, temperature, pressure, humidity, etc., of, by, and/or nearby to the instrument arm assembly. When an instrument arm assembly (such as 130, 140) comprises one or more illumination sources, cameras, haptic and/or force feedback instruments, and/or other sensors and/or instruments, as described above, the instrument arm assembly may also comprise a gas shield, such as the gas shield 127a described above for the camera arm assembly 120. One or more of the instrument arm assemblies (such as 130, 140) may further comprise one or more internal temperature control assemblies operable to control (such as reduce or increase) the temperature of one or more components of the instrument arm assembly.

Figure 7A:
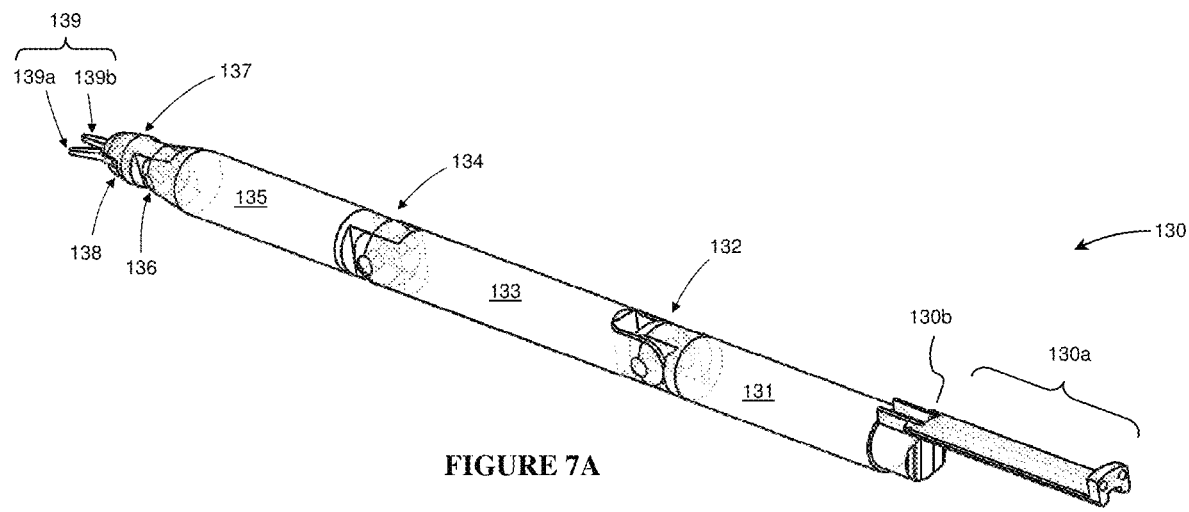
FIG. 7A is an illustration of a perspective view of an example embodiment of an instrument arm assembly.
Figure 7B:
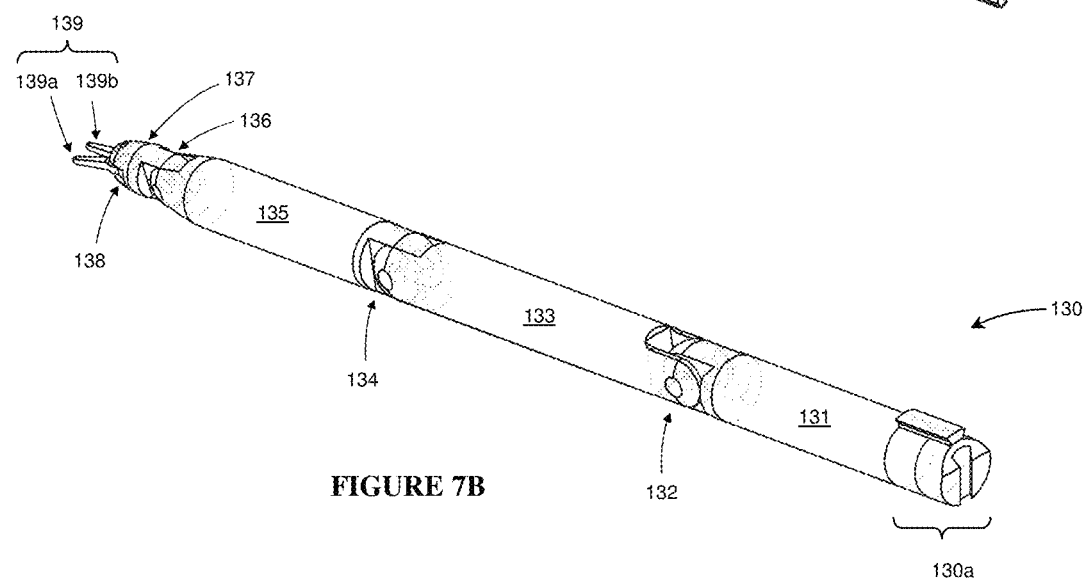
FIG. 7B is an illustration of a perspective view of another example embodiment of an instrument arm assembly.

As illustrated in the example embodiment of FIG. 1 and FIGS. 7A and 7B, each of the instrument arm assemblies, including the first instrument arm assembly 130, may comprise a first instrument arm segment 131, a second instrument arm segment 133, a third instrument arm segment 135, and a fourth instrument arm segment 137. The instrument arm assembly 130 may also comprise a first joint portion 132, a second joint portion 134, a third joint portion 136, and an instrument joint portion 138. Each of the aforementioned joint portions may be configurable, either manually and/or via the computing device (or system), to provide an attached instrument arm segment (and the end instrument 139, including instruments 139a and 139b) with one or more in vivo degrees of freedom when the instrument arm assembly is provided in the abdominal cavity of the patient. For example, the first joint portion 132 may be operable to provide the second instrument arm segment 133 with a pivotal movement relative to the first joint portion 132, as illustrated by arrow A in FIG. 1, and/or a torsional movement relative to the first joint portion 132, as illustrated by arrow B in FIG. 1. As another example, the second joint portion 134 may be operable to provide the third instrument arm segment 135 with a torsional movement relative to the second joint portion 134, as illustrated by arrow C in FIG. 1, and/or a pivotal movement relative to the second joint portion 134, as illustrated by arrow F in FIG. 1. As another example, the third joint portion 136 may be operable to provide the fourth instrument arm segment 137 with a pivotal movement relative to the third joint portion 136, as illustrated by arrow E in FIG. 1, and/or a torsional movement relative to the third joint portion 136, as illustrated by arrow F in FIG. 1. As another example, the instrument joint portion 138 may be operable to provide the instrument 139a with one or more pivotal movements relative to the instrument joint portion 138, as illustrated by arrow G in FIG. 1, and/or a torsional movement relative to the instrument joint portion 138 (not shown). As another example, the instrument joint portion 138 may be operable to provide the instrument 139b with one or more pivotal movements relative to the instrument joint portion 138, as illustrated by arrow G in FIG. 1, and/or a torsional movement relative to the instrument joint portion 138 (not shown). Accordingly, one or more of the instrument arm assemblies may be configurable, either manually and/or via the computing device (or system), to provide seven or more in vivo degrees of freedom and, together with the at least one in vitro degree of freedom provided by the port assembly 110, including the controllable swivel assembly 1300 (see FIG. 13), the one or more of the instrument arm assemblies may be configurable, either manually and/or via the computing device (or system), to provide a total of eight or more degrees of freedom. It is recognized herein that the aforementioned at least seven in vivo degrees of freedom for the instrument arm assembly enables at least the full range of natural movements by a surgeon's arm (via a computer-human interface, such as the example illustrated in FIG. 12) to be substantially directly mapped and/or translated to the instrument arm assembly, which is not achievable in present surgical robotic systems.

Each joint portion, including joint portions 132, 134, and 136, and instrument joint portion 138 may comprise any one or more configurations of gears and/or gear assemblies, including straight gear configurations, planetary gear configurations, beveled gear configurations, spiral beveled gear configurations, hypoid gear configurations, helical gear configurations, worm gear configurations, and/or any other gear configuration without departing from the teachings of the present disclosure. In example embodiments, each instrument arm assembly may also comprise one or more internal motors (not shown), or the like, operable to actuate the gears of each joint portion, including joint portions 132, 134, and 136, and/or the instrument arm segments 131, 133, 135, and 137. In this regard, each of the abovementioned motors, joint portions, and/or instrument arm segments may be operable to communicate, such as receive control commands and/or transmit information, from and/or to the computing device (or system) of one or more nearby and/or remotely located surgical teams 1204 via wired and/or wireless communication in example embodiments. Furthermore, each of the abovementioned motors, joint portions, and/or instrument arm segments may be operable to receive power from an external power source and/or the computing device (or system) via wired and/or wireless transmissions in example embodiments.

Each of the instrument arm assemblies may also comprise an instrument anchoring portion 130a operable to attach (or secure) the instrument arm assembly to one or more anchoring portions 116 (and/or flaps 116a), and this may be provided via the first instrument arm segment 131. FIG. 7A illustrates an example embodiment of an instrument anchoring portion 130a operable to attach to the anchoring portion 116 of the example embodiment of the port assembly 110 in FIG. 6A, and FIG. 7B illustrates an example embodiment of an instrument anchoring portion 130a operable to attach to the flaps 116a of the example embodiment of the port assembly 110 in FIG. 6C. These and other types or configurations of instrument anchoring portions 130a and anchoring portions 116 may be provided and configured in example embodiments without departing from the teachings of the present disclosure.

One or more internal temperature control assemblies (not shown) may be provided for each of the one or more instrument arm assemblies. Each internal temperature control assembly may be operable to control (such as reduce) the temperature and/or heat emission of the aforementioned gears and/or gear assemblies, motors, instrument joint portions (such as 132, 134, and 136), and/or instrument arm segments (such as 131, 133, 135, and 137). The one or more internal temperature control assemblies may also be operable to control (such as increase or decrease) the temperature of the instrument 139 (which may be desirable when the instrument 139 is a cutting tool, or the like). In an example embodiment, the one or more internal temperature control assemblies may be operable to perform such temperature control using one or more gases, liquids, and/or solids. For example, the gases and/or liquids may be fed, maintained, and/or regulated using an external source via one or more tubes, or the like. The one or more tubes used to provide, regulate, and/or discharge the gases and/or liquids may have a diameter between about 0.5 mm to 3 mm in example embodiments, but the dimensions of such tubes may also be more or less. It is to be understood in the present disclosure that the one or more tubes (if used), as well any solids (if used), may be provided through an interior of the instrument arm assembly without increasing dimensions (such as diameter) of the instrument arm assembly.

When the internal temperature control assembly utilizes gases, or the like, example embodiments may also be operable to provide such gases into the body cavity and/or discharge or recycle such gases outside of the body cavity via one or more tubes, or the like. The gases may comprise carbon dioxide, oxygen, and/or other gases in example embodiments. Such gases may be further operable to assist in providing and/or maintaining insufflation of the body cavity, such as via an opening (not shown).

When the internal temperature control assembly utilizes liquids, or the like, example embodiments may be operable to discharge or recycle such liquids outside of the body cavity.

When the internal temperature control assembly utilizes solids, or the like, such solids may possess properties that enable the surgical team to change the temperature of the solids, such as by applying electricity or other form of energy, so as to control (such as reduce) the temperature and/or heat emission of one or more components of the camera arm assembly 120.

In example embodiments, the internal temperature control assembly may utilize a combination of gases, liquids, solids, and/or the like without departing from the teachings of the present disclosure.

After the instrument arm assembly 130 has been inserted and attached (or secured) to the port assembly 110, the end instrument 139 may be configurable, either manually and/or via the computing device (or system), to apply between about 0 to 20 N of force when performing surgical actions and procedures, such as clipping and/or grasping actions. Furthermore, the end instrument 139, including each instrument 139a and 139b, may be configurable, either manually and/or via the computing device (or system), to apply between about 0 to 10 N of force when performing other surgical actions and procedures, such as translational, twisting, pulling, and/or pushing actions. It is to be understood in the present disclosure that the above range of applicable force are merely an illustration of example embodiments, and as such the range of applicable force may be smaller or larger than those recited above without departing from the teachings of the present disclosure.

In an example embodiment, the instrument arm segments, including the first instrument arm segment 131, the second instrument arm segment 133, the third instrument arm segment 135, and/or the fourth instrument arm segment 137, may be substantially cylindrical in shape, as illustrated in at least FIGS. 7A and 7B. The instrument arm segments, including the first instrument arm segment 131, the second instrument arm segment 133, the third instrument arm segment 135, and/or the fourth instrument arm segment 137, may also be formed in any one of a plurality of other shapes, sizes, and/or dimensions without departing from the teachings of the present disclosure.

In an example embodiment, the instrument anchoring portion 130*a* may be attachable to the rest of the instrument arm assembly 130, such as via the first instrument arm segment 131, via hinge joint 130*b*, or the like, and the instrument arm anchoring portion 130*a* may be of sufficient length and thickness, such as about 80 to 130 mm in length, about 3-15 mm in width, and about 0.2 to 3 mm in thickness, to attach (or connect or anchor) to one or more anchoring portions 116 and/or flaps 116*a*.

Figure 11A:
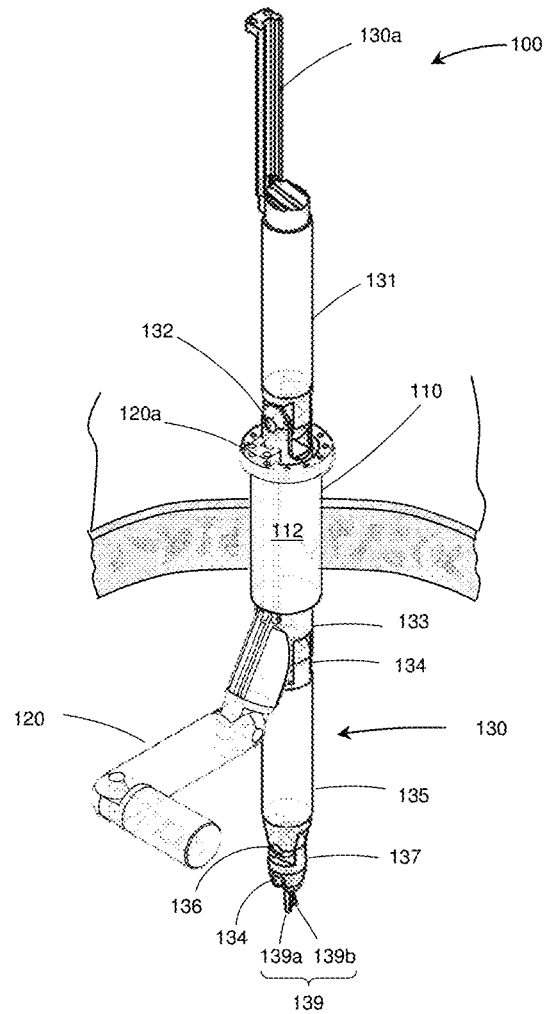
FIG. 11A is an illustration of a perspective view of an example embodiment of a surgical device being configured with an instrument arm assembly.
Figure 11B:
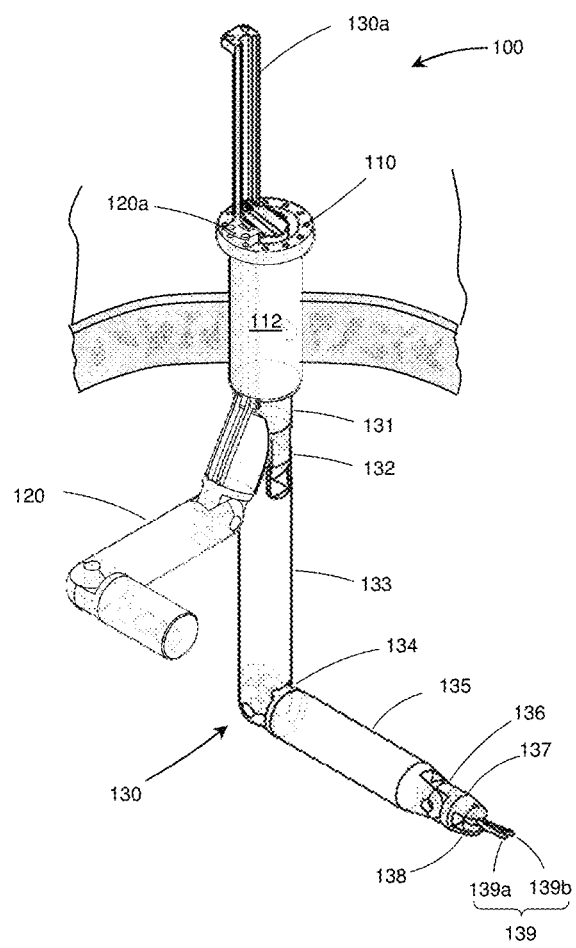
FIG. 11B is another illustration of a perspective view of an example embodiment of a surgical device being configured with an instrument arm assembly.
Figure 11C:
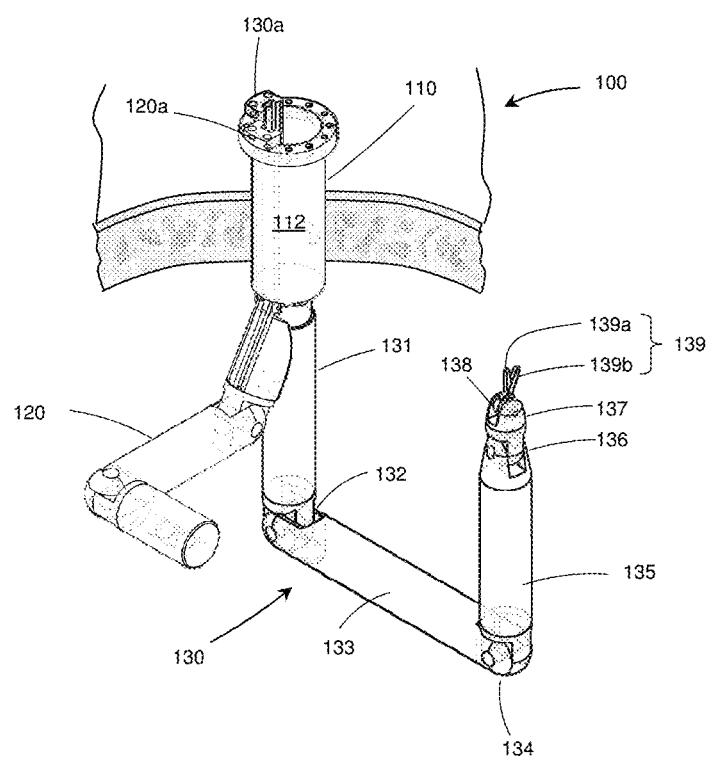
FIG. 11C is another illustration of a perspective view of an example embodiment of a surgical device being configured with an instrument arm assembly.
Figure 11D:
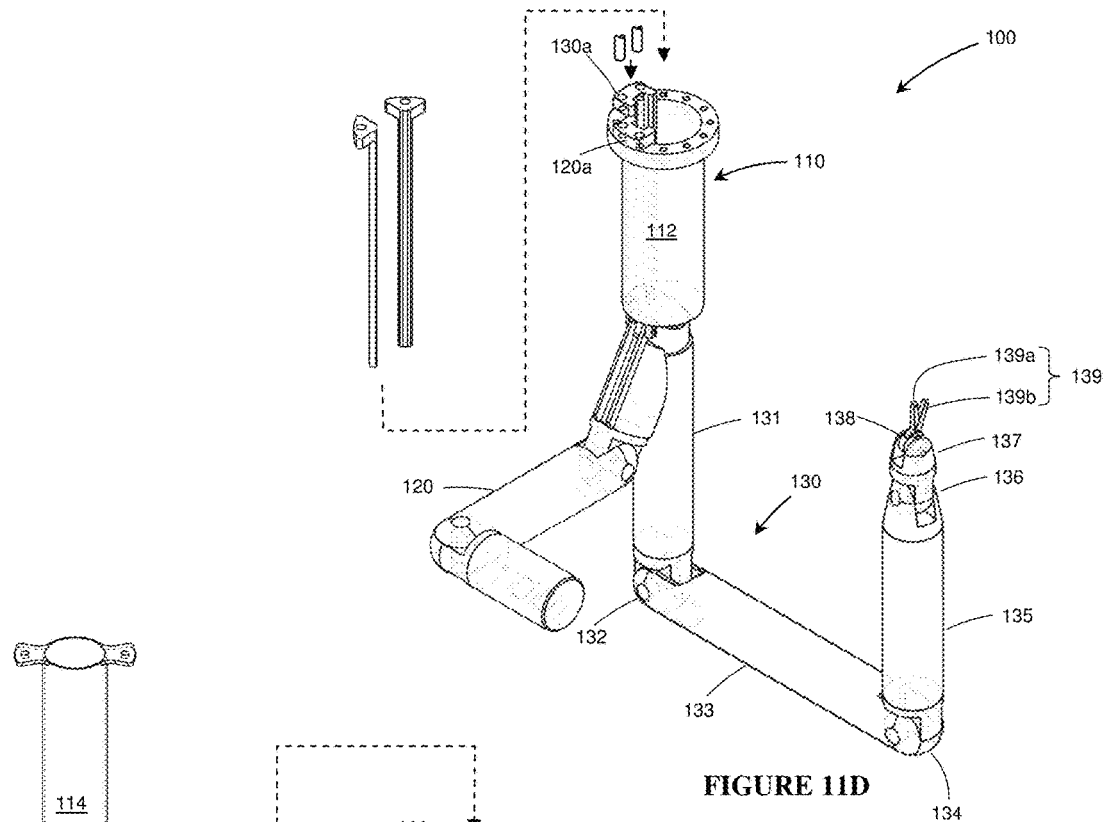
FIG. 11D is another illustration of a perspective view of an example embodiment of a surgical device being configured with an instrument arm assembly.

After the instrument arm assembly 130 is inserted through the port assembly 110 and into an abdominal cavity of a patient, the instrument anchoring portion 130*a* may be securely received by the port assembly 110 via anchoring portions 116 and/or flaps 116*a*. To enable the insertion (and removal) of other instruments, such as one or more other instrument arm assemblies 140, the instrument arm assembly 130 may be positionable in such a way that a clear path (via the first access port 112*a* and/or second access port 114*a* of the port assembly 110) may be provided to allow the insertion (and removal) of other instruments (see, for example, FIG. 11E). Such positioning may be secured by the use of one or more supporting pins 117. The support pins 117 may be provided in the form of curved plates, as illustrated in FIG. 6D and FIG. 11D, or other shapes and forms. In example embodiments, such supporting pins 117 may also be operable to provide a separation or isolation of any cables and tubes (not shown) from the opening portion of the first access port 112*a* and/or second access port 114*a* of the port assembly 110.

In example embodiments, the supporting pins 117 may be provided so as to not only secure the position of the instrument arm assembly 130 in such a way as to allow insertion (and removal) of other instruments, but to also secure the position of the instrument arm assembly 130 so as to allow removal (and insertion) of the instrument arm assembly 130 itself. As previously explained above for FIGS. 6F and 6G, the port assembly 110 may comprise a plurality of receiving sections 117' for support pins 117 (see first illustration of FIGS. 6F and 6G). One of the receiving portions 117*a*' may be operable to receive a support pin 117*a* to securely position one of the flaps 116*a* of the port assembly 110 (and thus securely position an arm assembly, such as a camera arm assembly, instrument arm assembly, or an assistant arm assembly) in an engaged position, as illustrated in the second illustration of FIG. 6F. To securely position the flap 116*a* of the port assembly 110 (and thus vertically position an arm assembly, such as a camera arm assembly, instrument arm assembly, or assistant arm assembly) in a transitionable position, as illustrated in the second illustration of FIG. 6G, a support pin 117*b* may be provided in receiving portion 117*b*'.

Figure 7C:
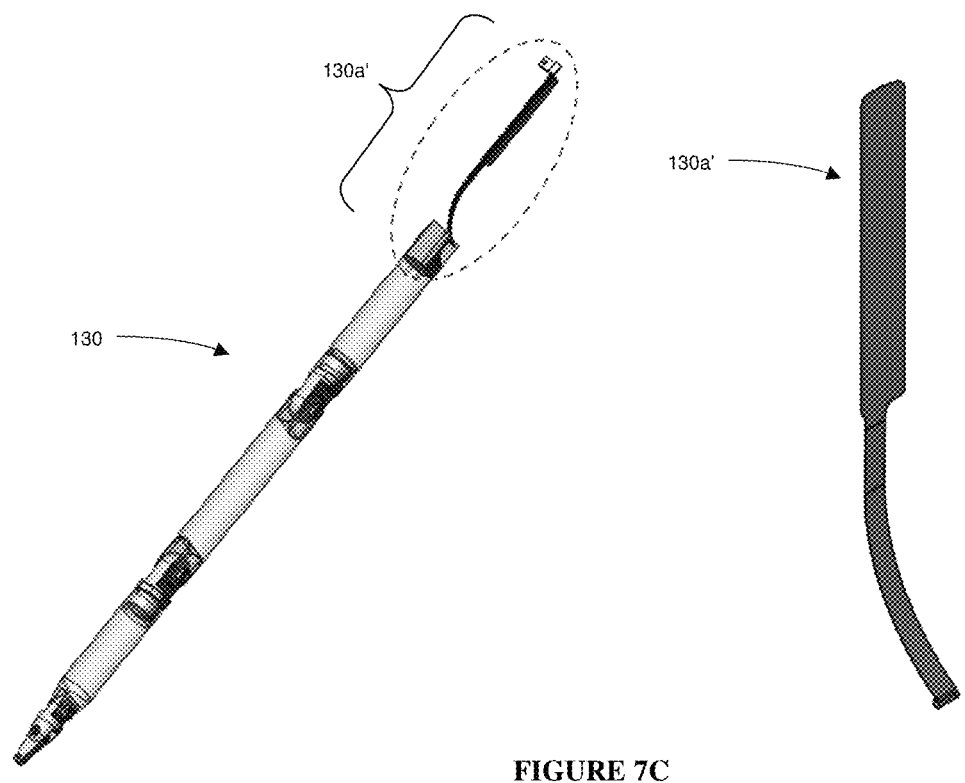
FIG. 7C is an illustration of a perspective view of an example embodiment of an instrument arm assembly with an instrument anchoring portion.
Figure 7D:
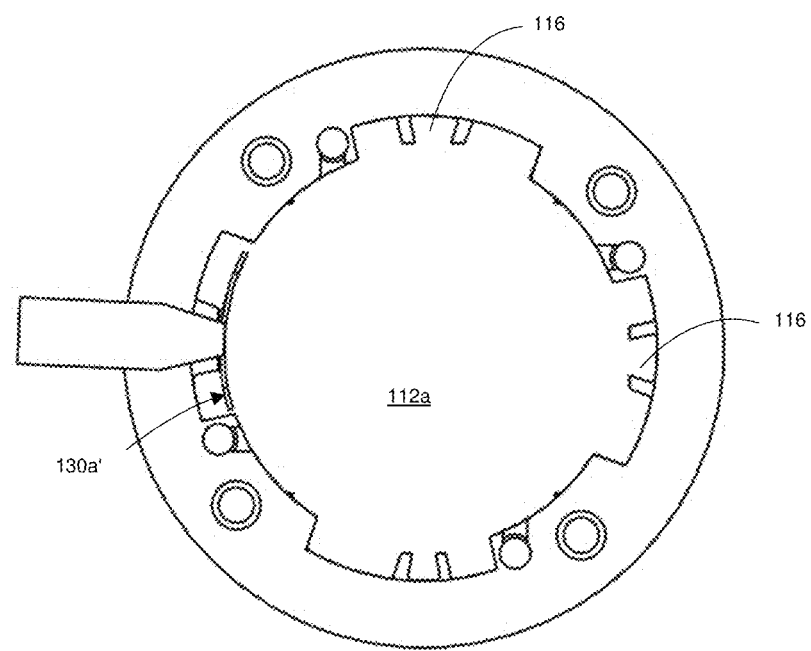
FIG. 7D is an illustration of a top view of an example embodiment of an instrument anchoring portion of an instrument arm assembly anchored to an interior of a port assembly, along with cabling provided between the instrument anchoring portion and the port assembly.
Figure 7E:
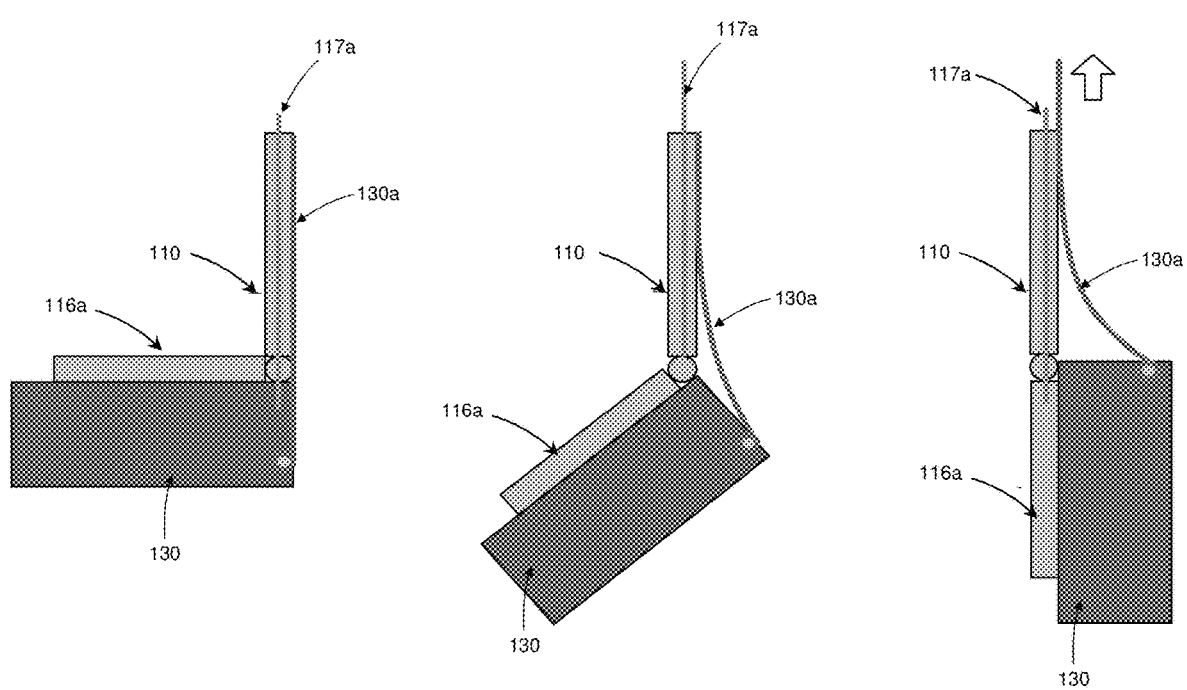
FIG. 7E is an example illustration of a perspective view of an example embodiment of an instrument arm assembly positioned in an engaged position, an instrument arm assembly being transitioned, and an instrument arm assembly positioned in a transitionable position.

Example embodiments of the instrument anchoring portion 130*a*', such as those illustrated in FIGS. 7C-E, may comprise at least a restorative portion 130*a*", or the like, which may be a portion of the instrument anchoring portion 130*a*' that is slightly curved in shape when in its natural shape/position (see, for example, FIG. 7C). The restorative portion 130*a*" may provide a restoring force, such as a spring-like elastic force, when the restorative portion 130*a*" of the instrument anchoring portion 130*a*' is deviated from its natural shape/position. For example, if an external force is applied to the restorative portion 130*a*" of the instrument anchoring portion 130*a*' so as to result in the overall shape of the instrument anchoring portion 130*a*' deviating from its natural shape/position (such as being brought to a substantially straight shape), and the external force is then removed, the restoring force of the restorative portion 130*a*" of the instrument anchoring portion 130*a*' may be operable to cause the instrument anchoring portion 130*a*' to return to its natural shape/position, as illustrated in FIG. 7C. It is recognized in the present disclosure that such an embodiment of the instrument anchoring portion 130*a*' may enable a safe and effective insertion and/or removal of the instrument arm assembly 130 into and/or from the body cavity of a patient. For example, as illustrated in the sequence of illustrations of FIG. 7E, an instrument arm assembly 130 securely positioned in an engaged position via supporting pins 117*a* (left illustration of FIG. 7E) may be changed to be in a transitionable position by removing the support pins 117*a* (middle illustration of FIG. 7E), which enables the restoring forces of the instrument anchoring portion 130*a*' to return the instrument anchoring portion 130*a*' to its natural shape/position and position the instrument arm assembly 130 for removal or insertion (right illustration of FIG. 7E).

In an example embodiment, the length of the first instrument arm segment 131 may be between about 60 to 85 mm, the length of the second instrument arm segment 133 may be between about 80 to 105 mm, the length of the third instrument arm segment 135 may be between about 65 to 90 mm, the length of the fourth instrument arm segment 137 may be between about 5 to 30 mm, and the overall length of the collective instrument arm (excluding the instrument 139*a* and 139*b*) may be between about 210 to 310 mm. In example embodiments, the length of the first instrument arm segment 131 may be between about 70 to 80 mm, the length of the second instrument arm segment 133 may be between about 90 to 100 mm, the length of the third instrument arm segment 135 may be between about 75 to 85 mm, the length of the fourth instrument arm segment 137 may be between about 15 to 25 mm, and the overall length of the collective instrument arm (excluding the end instrument 139 and instrument 139*a* and 139*b*) may be between about 250 to 290 mm. In example embodiments, a length of one or more of the instrument arm segments and/or the end instrument 139 may also be adjustable by the computing device (or system) of one or more nearby and/or remotely located surgical teams 1204 before, during, and/or after insertion of the instrument arm assembly into the cavity of the patient. The outer diameter of one or more of the instrument arm segments may be about 10 to 16 mm. In an example embodiment, the outer diameter of one or more of the instrument arm segments may be about 16 mm.

Each of the instrument arm assemblies, including the first instrument arm segment 131, the second instrument arm segment 133, the third instrument arm segment 135, the fourth instrument arm segment 137, the end instrument 139, the first joint portion 132, the second joint portion 134, the third joint portion 136, the instrument joint 138, the instrument arm anchoring portion 130a, and/or the hinge joint 130b, may be formed using any one or more of a plurality of materials, such as surgical-grade metals, high-strength aluminum alloys, stainless steel (such as 304/304L, 316/316L, and 420), pure titanium, titanium alloys (such as Ti6Al4V, NiTi), and cobalt-chromium alloys. It is to be understood in the present disclosure that other materials may also be used without departing from the teachings of the present disclosure.

Method of Setting up the Surgical Device

Figure 9:
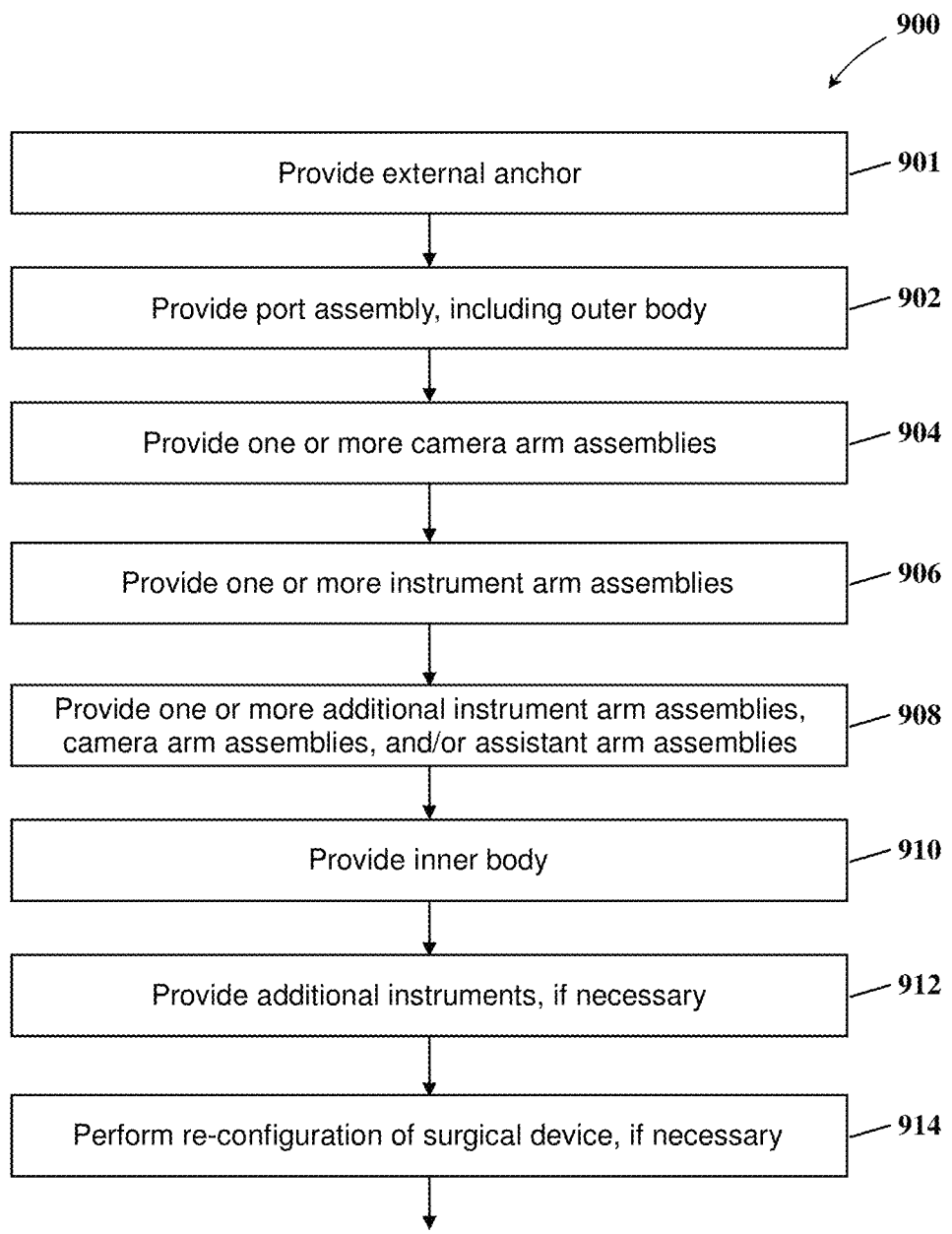
FIG. 9 is a flow diagram of an exemplary method for configuring a surgical device.

As illustrated in FIG. 9, example embodiments of the surgical device 100 may be configurable to perform a surgical action or procedure in one of a plurality of ways. In an example embodiment, the external anchor 200 may be provided and installed/anchored (e.g., action 901) to the stationary object. After providing the opening (such as an incision or a natural orifice) and a workable space in abdominal cavity (such as via insufflation using $CO_2$ and/or other gases, vacuum suction tools, and/or retractable hook tools) for the patient, the port assembly 110 may be provided, inserted, and installed (e.g., action 902) in or about the opening of the patient using the external anchor 200. The controllable swivel assembly 1300 may also be used in example embodiments. For example, a single incision through the umbilicus and a workable abdominal cavity of about 10-12 cm in height may be provided for the patient. Thereafter, one or more camera arm assemblies (e.g., action 904), one or more instrument arm assemblies (e.g., action 906), and/or one or more assistant arm assemblies (e.g., action 908) may be inserted into the port assembly 110, inserted and configured in the abdominal cavity of the patient, and attached to the anchoring portions 116 and/or flaps 116a of the port assembly 110. A surgical action or procedure may then be performed in any part, area, and/or quadrant of the abdominal cavity of the patient using the surgical device 100. These processes will now be described with references to at least FIGS. 9, 10A-D, 11A-E, and 12.

(1) Providing the External Anchor and Installing the Outer Body of the Port Assembly (e.g., Actions 901 and 902).

In an example embodiment, the external anchor 200 may be provided and installed/anchored to one or more stationary objects, such as a side rail 300 of a surgical table/bed, as illustrated in FIGS. 2A and 2B. One or more segments 202, 206, 210, and 214 of the external anchor 200 may cooperate using one or more joints 204, 208, 212, and 216 of the external anchor 200 to fix the position (including orientation) of the port assembly 110 in or about the opening of the patient.

In an example embodiment, as illustrated in FIG. 13, the external anchor 200 may comprise a controllable swivel assembly 1300 operable to provide one or more additional in vitro degrees of freedom, such as via a first swivel portion 1302, second swivel portion 1304, and/or third swivel portion 1306. The controllable swivel assembly 1300 may further comprise a motor 1302a for the first swivel portion 1302, a motor 1304a for the second swivel portion 1304, a motor 1306a for the third swivel portion 1306, one or more supporting arms 1308, and one or more locks 1310.

The first swivel portion 1302 may be operable to provide, as one of the in vitro degrees of freedom, a translational movement of the port assembly 110 along an axis defined by the elongated length of the port assembly 110, as illustrated by the arrow A. In example embodiments, the translational movement, as illustrated by arrow A, provided by the first swivel portion 1302 may be between about 0 to 50 mm.

The controllable swivel assembly 1300 may further comprise a second swivel portion 1304 operable to provide, as another one of the in vitro degrees of freedom, a torsional or rotational movement of the port assembly 110 about an axis depicted by axis Y. In example embodiments, the torsional or rotational movement, as illustrated by the arrow B, provided by the second swivel portion 1304 may be between about +/−180 degrees.

The controllable swivel assembly 1300 may further comprise a third swivel portion 1306 operable to provide, as another one of the in vitro degrees of freedom, a pivotal or rotational movement of the port assembly 110 about an axis perpendicular to the Y-axis, such as the axis depicted by axis Z (which comes out of the page). In example embodiments, the Z-axis or the center of rotation may be located at about opening of the patient, such as at the mid-point of the abdominal wall. In example embodiments, the pivotal or rotational movement, as illustrated by the arrow C, provided by the third swivel portion 1306 may be between about +/−80 degrees.

It is recognized in the present disclosure that the controllable swivel assembly 1300 may comprise the first swivel portion 1302, second swivel portion 1304, and/or third swivel portion 1306 in example embodiments. The controllable swivel assembly 1300 may further comprise other swivel portions (not shown) when more than three in vitro degrees of freedom and/or movements/rotations other than those providable by the first swivel portion 1302, second swivel portion 1304, and third swivel portion 1306 are desired and/or required.

The controllable swivel assembly 1300, including the first swivel portion 1302, the second swivel portion 1304, and/or the third swivel portion 1306, may be controllable either locally or remotely by the surgical team.

In an example embodiment illustrated in FIGS. 6A and 6B, the first end 112c may be inserted into a single opening of the patient, such as an incision through the umbilicus, and the second end 112b may be attached to the external anchor connector 216 to fix the outer body 112 in position (including orientation) with respect to at least the one or more stationary objects. Once fixed in position, the outer body 112 of the port assembly 110 may be operable to provide an access port (or passageway) via the first access port 112a for insertion of one or more instruments.

In example embodiments, one or more of the instrument arm assemblies, camera arm assemblies, and/or assistant arm assemblies may be operable to communicate with the computing device (or system) of one or more nearby and/or remotely located surgical teams 1204, including receive and/or transmit, one or more of control, imaging, feedback, information, and/or power signals using wired and/or wireless communication. For wired communication, one or more external wires (i.e. in example embodiments wherein an instrument communicates using wires and the wires are not provided and/or embedded substantially inside the instrument), one or more interior portions of the first access port 112a may be provided with one or more channels, grooves, or the like, to allow for the one or more wires to be routed through the port assembly 110. It is to be understood herein that one or more channels, grooves, or the like, may also be provided for one or more exterior portions of the inner body 114 in addition to or in replacement of those provided for the one or more interior portions of the first access port 112a in such example embodiments. In example embodiments wherein communications, including receiving and transmitting, are provided via wireless communication, such channels, grooves, or the like, may not be required.

(2) Inserting and Attaching the Camera Arm Assembly (e.g., Action 904).

Figure 10A:
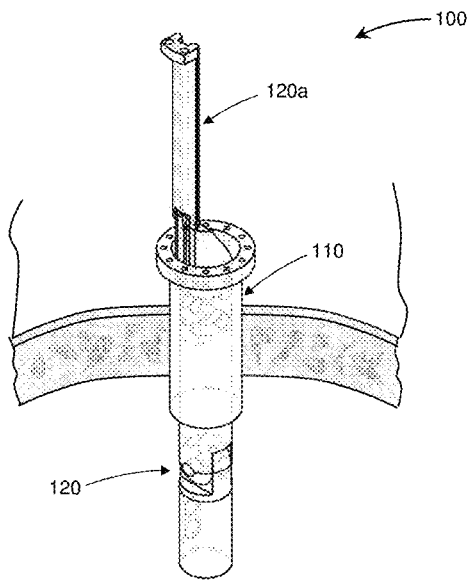
FIG. 10A is an illustration of a perspective view of an example embodiment of a surgical device being configured with a camera arm assembly.
Figure 10B:
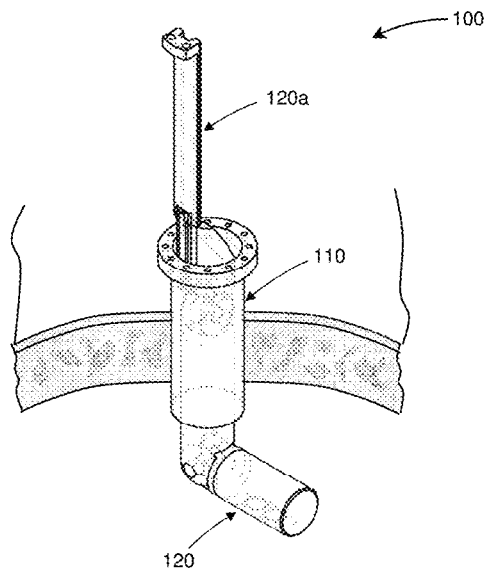
FIG. 10B is another illustration of a perspective view of an example embodiment of a surgical device being configured with a camera arm assembly.
Figure 10C:
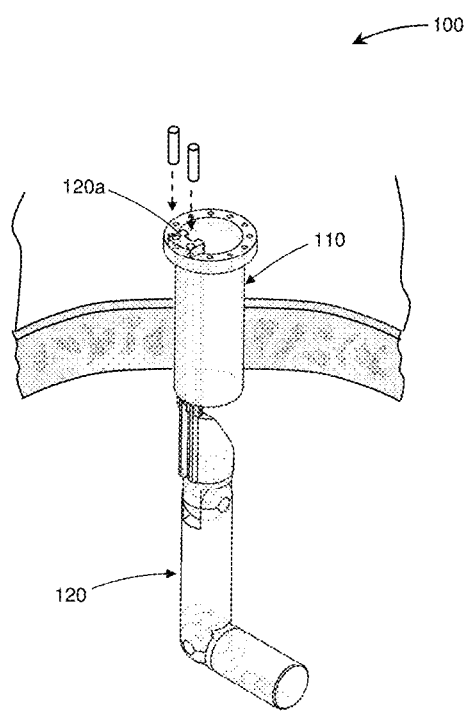
FIG. 10C is another illustration of a perspective view of an example embodiment of a surgical device being configured with a camera arm assembly.
Figure 10D:
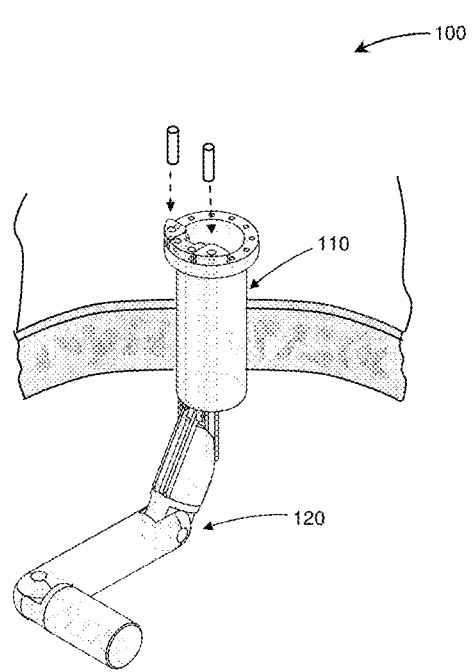
FIG. 10D is another illustration of a perspective view of an example embodiment of a surgical device being configured with a camera arm assembly.

After the outer body 112 of the port assembly 110 is fixed in position (including orientation) in or about the opening of the patient, the camera arm assembly 120 may be inserted into the port assembly 110, such as via the first access port 112a, and into the abdominal cavity of the patient, as illustrated in FIGS. 10A-D. The camera arm assembly 120 may be dynamically configured (that is, configured before, during, and/or after the insertion of the camera arm assembly 120 into the abdominal cavity of the patient), either manually and/or by commanding via the computing device (or system) of one or more nearby and/or remotely located surgical teams 1204, by actuating one or more of the camera joint portions 122, 124, 126 and/or camera arm segments 121, 123, 125 in such a way as to prevent a portion of the camera arm assembly 120 from contacting with an interior wall of the abdominal cavity of the patient. Furthermore, the said configuring before, during, and/or after the insertion may also be performed so as to provide a subsequent clear passageway into the abdominal cavity of the patient, as illustrated in FIG. 10D, for one or more subsequent insertions of other instruments, such another camera arm assembly, one or more instrument arm assemblies, and/or one or more assistant arm assemblies. The camera arm assembly 120 may also be anchored to the port assembly 110, as illustrated in FIG. 10C, using one or more anchoring portions 116 and/or flaps 116a. In example embodiments, the camera anchoring portion 120a of the camera arm assembly 120 may be operable to anchor or secure to the port assembly 110 via one or more anchoring portions 116 and/or the flap 116a of the port assembly 110, as described above and herein.

In example embodiments, the camera arm assembly 120 may be the first instrument installed after the installation of the outer body 112 of the port assembly 110. In installing the camera arm assembly 120 first and positioning the camera in the abdominal cavity of the patient in such a way as to provide an operator (such as the surgeon) with an interior cavity view of subsequent insertion(s) of other instrument(s) (including another camera arm assembly, one or more instrument arm assemblies, and/or one or more assistant arm assemblies), it is recognized in the present disclosure that the operator, either manually and/or via the computing device (or system), may be enabled to properly and carefully perform dynamic configuring of the subsequent instruments during and after the insertion of the subsequent instruments into the abdominal cavity of the patient. As a result, the operator may avoid and/or prevent such subsequent instruments from contacting with and/or affecting a part of an interior of the abdominal cavity (and/or other arm assemblies) and possibly causing unintentional and undesirable harm, injury, and/or complications to the patient. It is to be understood in the present disclosure that the instrument arm assembly 120, the assistant arm assembly 150, or other instruments may also be the first instrument installed after the installation of the outer body 112 of the port assembly 110 without departing from the teachings of the present disclosure.

(4) Inserting and Attaching a First Instrument Arm Assembly (e.g., Action 906).

Figure 11E:
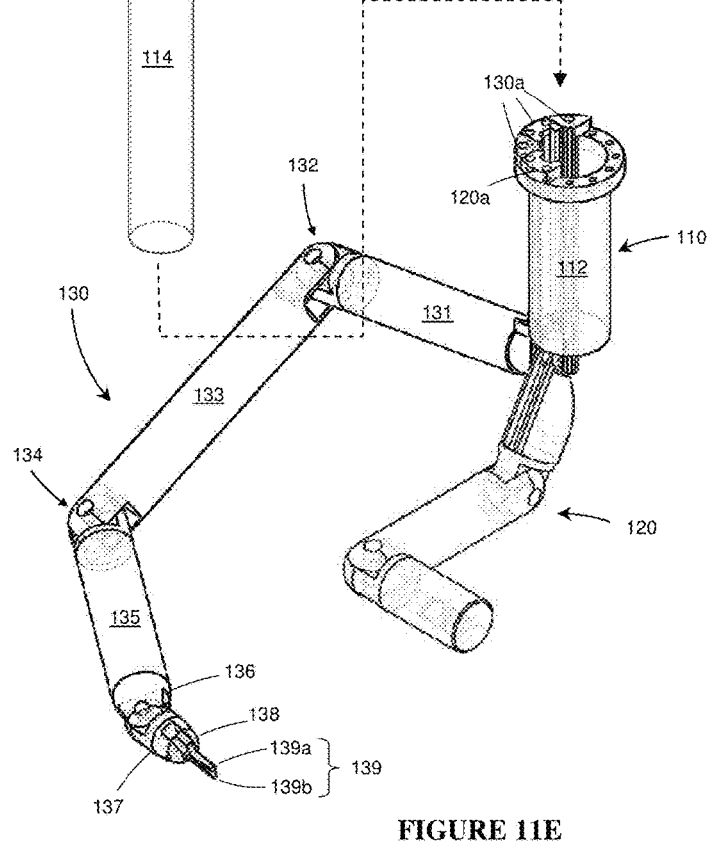
FIG. 11E is another illustration of a perspective view of an example embodiment of a surgical device being configured with an instrument arm assembly.

An instrument arm assembly 130 may be inserted into the port assembly 110, such as via the first access port 112a, and into the abdominal cavity of the patient, as illustrated in FIGS. 11A-E. The instrument arm assembly 130 may be dynamically configured (that is, configured before, during, and/or after the insertion of the instrument arm assembly 130 into the cavity of the patient), either manually and/or by commanding via the computing device (or system) of one or more nearby and/or remotely located surgical teams 1204, by actuating one or more of the joint portions 130b, 132, 134, 136, 138 and/or instrument arm segments 131, 133, 135, 137 and/or end instrument 139, including instruments 139a and 139b, in such a way as to prevent a portion of the instrument arm assembly 130 from contacting with an interior wall of the abdominal cavity of the patient. Furthermore, the said configuring before, during, and/or after the insertion may also be performed so as to provide a clear passageway into the abdominal cavity of the patient, as illustrated in FIG. 11E, for one or more subsequent insertions of other instruments, such one or more camera arm assemblies, one or more additional instrument arm assemblies, and/or one or more assistant arm assemblies. The instrument arm assembly 130 may also be anchored to the port assembly 110, as illustrated in FIG. 11D, using one or more anchoring portions 116 and/or flaps 116a. In example embodiments, the instrument anchoring portion 130a of the instrument arm assembly 130 may be operable to anchor or secure to the port assembly 110 via one or more anchoring portions 116 and/or the flap 116a of the port assembly 110, as described above and herein.

(5) Inserting and Attaching One or More Additional Instrument Arm Assemblies, One or More Assistant Arm Assemblies, and/or One or More Additional Camera Arm Assemblies (e.g., Action 908).

One or more additional instrument arm assemblies (such as 140 illustrated in FIGS. 3A, 3B, 4, and 5), one or more assistant arm assemblies (such as 150 illustrated in FIGS. 3A, 3B, 4, and 5), and/or one or more additional camera arm assemblies (not shown) may also be inserted into the port assembly 110, such as via the first access port 112a, and into the cavity of the patient. The one or more instrument arm assemblies, one or more assistant arm assemblies, and/or one or more additional camera arm assemblies may also be dynamically configured, either manually and/or via the computing device (or system), in substantially the same way as described above so as to prevent a portion of the assemblies from contacting with an interior wall of the abdominal cavity of the patient. Furthermore, the said configuring during and/or after the insertion may also be performed so as to provide a clear passageway into the abdominal cavity of the patient for one or more subsequent insertions of other instruments, such one or more camera arm assemblies, one or more additional instrument arm assemblies, and/or one or more assistant arm assemblies. The one or more additional instrument arm assemblies, one or more assistant arm assemblies, and/or one or more camera arm assemblies may also be attached to the port assembly 110 and prevented from blocking or partially blocking a passageway into the abdominal cavity of the patient for the subsequent insertions of other instruments. In example embodiments, an anchoring portion of the one or more additional instrument arm assemblies, one or more assistant arm assemblies, and/or one or more camera arm assemblies may be operable to anchor or secure to the port assembly 110 via one or more anchoring portions 116 and/or the flap 116a of the port assembly 110, as described above and herein.

(6) Providing the Inner Body of the Port Assembly and Other Additional Instruments (e.g., Action 910 and 912).

After the outer body 112 of the port assembly 110 is fixed in position (including orientation) in or about the opening of the patient and the one or more camera arm assemblies (such as camera arm assembly 120), the one or more instrument arm assemblies (such as instrument arm assemblies 130 and 140), and/or the one or more assistant arm assemblies (such as assistant arm assembly 150) have been installed and dynamically configured in the abdominal cavity of the patient, the inner body 114 of the port assembly 110 may be inserted into the first access port 112a and attached to one or more of the anchoring portions 116 of the outer body 112 (e.g., see FIGS. 6A and 6B). After the installation of the inner body 114, the inner body 114 may be operable to provide a second access port 114a for the surgical device 100. In example embodiments, the second access port 114a may be considered as replacing the first access port 112a of the surgical device 100. In example embodiments, the second access port 114a is operable to provide an access port having a consistently maintained diameter after the insertion and installation of the one or more camera arm assemblies (such as camera arm assembly 120), the one or more instrument arm assemblies (such as instrument arm assemblies 130 and 140), and/or the one or more assistant arm assemblies (such as assistant arm assembly 150). The consistently maintained diameter may be between about 15 to 17 mm in example embodiments.

The inner body 114 may be operable to assist with, support, and/or ensure the attachment of inserted instrument(s), including the one or more instrument arm assemblies, the one or more camera arm assemblies, and/or the one or more assistant arm assemblies. The inner body 114 may also be operable to isolate and/or protect one or more attachment portions of the inserted instrument(s), such as 120a and/or 130a. Furthermore, the inner body 114 may be operable to provide an access port (or passageway) via the second access port 114a so as to allow access to the abdominal cavity of the patient, including allowing the insertion of other instruments, such as instrument 160 (e.g., see FIG. 5). For example, during a surgical action or procedure, the second access port 114a may be operable to allow the insertion of a suction instrument 160 so as to allow for the removal of accumulative cavity fluids and/or gases, such as water and/or blood.

It is recognized in the present disclosure that example embodiments of the surgical device 100 and the methods 900 of configuring the surgical device 100 provided in the present disclosure for performing surgical procedures via a single opening of a patient may provide for several advantages and/or solutions to problems, including, but not limited to, a requirement for only a single opening instead of the multiple incisions required by known MIS procedures using surgical robotic systems; a substantial reduction in the size of the opening (such as an incision) of less than about 24 mm, as compared to present MIS procedures and known surgical robotic systems and procedures requiring between rather large incisions of about 30 to 35 mm; a reduction or improvement pertaining to excessive blood loss, wound sizes, number of wounds, healing times, pain, hospitalization periods as a result of the reduction in the number and sizes of incisions and prevention of instruments from contacting with an interior part of the abdominal cavity of the patient; enabling access all parts, areas, and quadrants of the abdominal cavity of the patient during and after installation and/or set up of the surgical device 100 as compared to the inability for known surgical robotic systems and methods to access all or even most parts, areas, and quadrants of the cavity of the patient during and after installation and/or set up; providing at least seven in vivo degrees of freedom for each instrument arm assembly (such as instrument arm assemblies 130 and 140) and a total of at least eight degrees of freedom (via the additional one or more in vitro degrees of freedom provided by the port assembly 110, including the controllable swivel assembly 1300) for each of the instrument arm assemblies; providing feedback, including haptic and/or force feedback, other feedback, and/or information/measurements via the other instruments and/or sensors, to the one or more local and/or remote surgical teams 1204 during installation and/or set up, during the surgical action or procedure, and after the surgical action or procedure; and providing a plurality of 2D and/or 3D standard or high definition views for all parts, areas, and quadrants of the abdominal cavity of the patient and each of the instruments provided in the abdominal cavity of the patient. Setup, installation, removal, control, operation, and/or monitoring of the surgical device 100 may be performable partially, entirely, and/or in cooperation with the surgical team system illustrated in FIG. 12.

(7) Re-configuring the Surgical Device (e.g., Action 914).

Before and/or after the insertion and installation of the inner body 114, the surgical device 100 may be re-configurable in one of a plurality of ways. For example, one or more of the installed instruments, including the one or more instrument arm assemblies, the one or more camera arm assemblies, and the one or more assistant arm assemblies, may be re-configured, re-positioned, and/or re-oriented, either manually and/or by the computing device (or system), via the plurality of in vivo degrees of freedom configurable by each installed instrument and/or the one or more in vitro degrees of freedom configurable by the external anchor 200 and the outer body 112 of the port assembly 110. In doing so, the one or more installed instruments may be operable to access other parts, areas, and/or quadrants of the abdominal cavity of the patient without a requirement to re-perform the set up process, as presently required in known surgical robotic systems.

The surgical device 100 may also be operable to add (and/or remove) one or more instruments (or installed instruments), such as one or more instrument arm assemblies, one or more camera arm assemblies, and/or one or more assistant arm assemblies, by removing the installed inner body 114 and/or installing (and/or removing) the required (or unrequired) instruments, as described above and herein. Once the desired addition (and/or removal) of the one or more instruments (or installed instruments) is performed, the inner body 114 may then be re-installed into the first access port 112a without a requirement to re-perform the set up process, as presently required in surgical robotic systems.

It is recognized in the present disclosure that the above-mentioned re-configuration, re-positioning, and/or re-orienting of the surgical device 100 on-the-fly before and/or during a surgical action or procedure enables surgical teams to complete surgical actions or procedures in a more efficient, effective, simplified, and safe manner.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, "assembly," "device," "portion," "segment," "member," "body," or other similar terms should generally be construed broadly to include one part or more than one part attached or connected together.

Various terms used herein have special meanings within the present technical field. Whether a particular term should be construed as such a "term of art" depends on the context in which that term is used. "Connected," "connecting," "attached," "attaching," "anchored," "anchoring," "in communication with," "communicating with," "associated with," "associating with," or other similar terms should generally be construed broadly to include situations where attachments, connections, and anchoring are direct between referenced elements or through one or more intermediaries between the referenced elements. These and other terms are to be construed in light of the context in which they are used in the present disclosure and as one of ordinary skill in the art would understand those terms in the disclosed context. The above definitions are not exclusive of other meanings that might be imparted to those terms based on the disclosed context.

As referred to in the present disclosure, a computing device, a processor, and/or a system may be a virtual machine, computer, node, instance, host, and/or device in a networked or non-networked computing environment. A networked computing environment may be a collection of devices connected by communication channels that facilitate communications between devices and allow devices to share resources. Also as referred to in the present disclosure, a computing device may be a device deployed to execute a program operating as a socket listener and may include software instances.

Resources may encompass any type of resource for running instances including hardware (such as servers, clients, mainframe computers, networks, network storage, data sources, memory, central processing unit time, scientific instruments, and other computing devices), as well as software, software licenses, available network services, and other non-hardware resources, or a combination thereof.

A networked computing environment may include, but is not limited to, computing grid systems, distributed computing environments, cloud computing environment, etc. Such networked computing environments include hardware and software infrastructures configured to form a virtual organization comprised of multiple resources that may be in geographically disperse locations.

Furthermore, the coverage of the present application and any patents issuing from the present application may extend to one or more communications protocols, including TCP/IP.

Words of comparison, measurement, and timing such as "at the time," "equivalent," "during," "complete," and the like should be understood to mean "substantially at the time," "substantially equivalent," "substantially during," "substantially complete," etc., where "substantially" means that such comparisons, measurements, and timings are practicable to accomplish the implicitly or expressly stated desired result.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically, a description of a technology in the "Background" is not to be construed as an admission that technology is prior art to any invention(s) in this disclosure. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A surgical device comprising:
a port assembly having an access port and a plurality of anchoring portions, the port assembly further including:
a plurality of separate internal channels distributedly formed around the access port, each internal channel parallel to the access port and formed in alignment with one of the anchor portions of the port assembly;
a camera arm assembly having at least one camera at a distal end, the camera arm assembly configurable to insert into the access port and attach to one of the anchoring portions;
an instrument arm assembly, the instrument arm assembly configurable to insert into the access port and attach to one of the anchoring portions of the port assembly, the instrument arm assembly having a serial arrangement including:
a shoulder section, the shoulder section forming a shoulder central axis;
a first arm section, a proximal end of the first arm section connected to a distal end of the shoulder section via a shoulder joint portion, the first arm section being an elongated body forming a first arm central axis;
an elbow joint portion, the elbow joint portion including an elbow pivotal joint connecting a distal end of the first arm section to a proximal end of a second arm section;
the second arm section, a proximal end of the second arm section connected to the distal end of the elbow joint portion, the second arm section being an elongated body forming a second arm central axis;
a wrist section, a proximal end of the wrist section connected to a distal end of the second arm section via a wrist joint portion;
at least one end instrument connected to a distal end of the wrist section via an end instrument joint portion; and
an instrument arm anchor segment having a proximal end and a distal end, the instrument arm anchor segment having an instrument arm anchor body and an instrument arm anchor portion at a proximal end of the instrument arm anchor body, a distal end of the instrument arm anchor body connected to a proximal end of the shoulder section, wherein the instrument arm anchor body is configurable to be inserted through one of the internal channels of the port assembly, wherein the instrument arm anchor portion is configurable to anchor to one of the anchoring portions of the port assembly when the instrument arm anchor body is housed in one of the internal channels of the port assembly, wherein the instrument arm anchor body is formed in such a way that a clear path through the access port of the port assembly remains available for insertion of other instrument arm assemblies when the instrument arm anchor body is housed in one of the internal channels of the port assembly and the instrument arm anchor portion is anchored to one of the anchoring portions of the port assembly;

wherein the instrument arm assembly is configurable to provide at least seven in vivo degrees of freedom after the instrument arm assembly is inserted through the access port of the port assembly, the instrument arm anchor body is housed in one of the internal channels of the port assembly, and the instrument arm anchor portion is anchored to one of the anchoring portions of the port assembly, wherein each of the at least seven in vivo degrees of freedom is a rotation relative to a linear axis, the at least seven in vivo degrees of freedom including:

a movement of the first arm section relative to the shoulder central axis;

a movement of the first arm section relative to an axis formed by the shoulder joint portion, the axis formed by the shoulder joint portion being different from the shoulder central axis;

a movement of the first arm section relative to the first arm central axis, the movement of the first arm section being a rotational movement of the first arm section relative to the first arm central axis;

a movement of the second arm section relative to an axis formed by the elbow pivotal joint of the elbow joint portion, the axis formed by the elbow pivotal joint being different from the first arm central second axis;

a movement of the wrist section relative to the second arm central axis;

a movement of the end instrument relative to an axis formed by the wrist joint portion, the axis formed by the wrist joint portion being different from the second arm central axis; and a movement of the end instrument relative to an axis formed by the end instrument joint portion, the axis formed by the end instrument joint portion being different from the axis formed by the wrist joint portion; and wherein the shoulder joint portion, elbow joint portion, wrist joint portion, and end instrument joint portion are each independently controllable.

2. The surgical device of claim 1, wherein each of the at least seven in vivo degrees of freedom is independently controllable by a computing device.

3. The surgical device of claim 1, wherein the instrument arm assembly is configurable to provide at least eight degrees of freedom.

4. The surgical device of claim 1, wherein the port assembly is fixably positionable in at least a portion of an opening of a patient in one of a plurality of positions via an external anchor and configurable to provide at least one in vitro degree of freedom, and wherein at least one of the in vitro degrees of freedom of the port assembly is a torsional movement or a pivotal movement relative to the external anchor.

5. The surgical device of claim 1, wherein the port assembly further comprises an outer body and an inner body, wherein the inner body is configurable to insert into and attach to the outer body, and wherein the outer body comprises a first end fixably positionable in at least a portion of an opening of a patient in one of a plurality of positions and a second end operable to attach to an external anchor.

6. The surgical device of claim 1, wherein the port assembly is configurable to allow the insertion of at least the camera arm assembly and the instrument arm assembly through the access port of the port assembly.

7. The surgical device of claim 1, wherein the port assembly is configurable to allow an insertion of instruments into a cavity of a patient via the access port when the surgical device is in operation.

8. The surgical device of claim 1, wherein the camera arm assembly is configurable in a serial arrangement including a plurality of camera arm segments, camera joint portions, and the at least one camera attached to one of the camera arm segments, wherein each camera joint portion is configurable to provide an attached camera arm segment with at least one degree of freedom, wherein the at least one degree of freedom of each attached camera arm segment includes a torsional movement or a pivotal movement relative to the camera joint portion, wherein the at least one degree of freedom of each attached camera arm segment is an in vivo degree of freedom, wherein the at least one degree of freedom of each attached camera arm segment is independently controllable by a computing device, wherein the camera arm assembly further comprises at least one illumination source, and wherein the at least one camera is a high definition 3D camera.

9. The surgical device of claim 1, further comprising one or more additional instrument arm assemblies, wherein each additional instrument arm assembly comprises a serial arrangement including a plurality of arm segments, a plurality of joint portions, and at least one end instrument attached to one of the arm segments by an instrument joint portion at a distal end, wherein each joint portion is configurable to provide an attached arm segment with at least one degree of freedom, wherein the instrument joint portion is configurable to provide the end instrument with at least one degree of freedom, and wherein each of the one or more additional instrument arm assemblies is configurable to insert into the access port and attach to one of the anchoring portions.

10. The surgical device of claim 1, further comprising one or more assistant arm assemblies having a serial arrangement including a plurality of assistant arm segments and an assistant arm joint portion connecting serially arranged assistant arm segments, wherein each assistant arm joint portion is configurable to provide an attached assistant arm segment with at least one degree of freedom, wherein each of the one or more assistant arm assemblies is configurable to insert into the access port and attach to one of the anchoring portions, and wherein each of the degrees of freedom of each of the instrument arm assemblies and the assistant arm assemblies are independently controllable.

11. The surgical device of claim 1, wherein the instrument arm assembly is further configured to provide a force and/or haptic feedback to a computing device.

12. The surgical device of claim 1, wherein a length of the first arm section and/or second arm section is variably adjustable in response to a command from a computing device.

13. The surgical device of claim 1, wherein at least one operation of the instrument arm assembly is controllable via wired and/or wireless communication from a computing device.

14. The surgical device of claim 1, wherein an outer diameter of the port assembly is less than or equal to about 22 mm.

15. The surgical device of claim 1, wherein an outer diameter of the instrument arm assembly is less than or equal to about 16 mm.

* * * * *